United States Patent
Yanagawa et al.

(10) Patent No.: US 9,365,513 B2
(45) Date of Patent: Jun. 14, 2016

(54) FULLERENE DERIVATIVE, AND METHOD OF PREPARING THE SAME

(71) Applicants: Yoshiki Yanagawa, Shizuoka (JP); Ryota Arai, Shizuoka (JP)

(72) Inventors: Yoshiki Yanagawa, Shizuoka (JP); Ryota Arai, Shizuoka (JP)

(73) Assignee: Ricoh Company, Ltd., Tokyo (JP)

( * ) Notice: Subject to any disclaimer, the term of this patent is extended or adjusted under 35 U.S.C. 154(b) by 0 days.

(21) Appl. No.: 14/557,898

(22) Filed: Dec. 2, 2014

(65) Prior Publication Data

US 2015/0158814 A1 Jun. 11, 2015

(30) Foreign Application Priority Data

Dec. 11, 2013 (JP) ................................. 2013-255722

(51) Int. Cl.
| | | |
|---|---|---|
| C07D 209/02 | (2006.01) | |
| C07D 409/04 | (2006.01) | |
| C07D 209/52 | (2006.01) | |
| C07D 409/14 | (2006.01) | |
| C07D 487/06 | (2006.01) | |
| H01L 51/00 | (2006.01) | |
| H01L 51/42 | (2006.01) | |

(52) U.S. Cl.
CPC ............. *C07D 209/52* (2013.01); *C07D 409/04* (2013.01); *C07D 409/14* (2013.01); *C07D 487/06* (2013.01); *H01L 51/0047* (2013.01); *H01L 51/0037* (2013.01); *H01L 51/0068* (2013.01); *H01L 51/0072* (2013.01); *H01L 51/4253* (2013.01); *Y02E 10/549* (2013.01)

(58) Field of Classification Search
CPC ............................ C07D 209/52; C07D 409/04
See application file for complete search history.

(56) References Cited

U.S. PATENT DOCUMENTS

2014/0024839 A1 1/2014 Yanagawa

FOREIGN PATENT DOCUMENTS

| JP | 2010-219448 | 9/2010 |
|---|---|---|
| JP | 2011-026235 | 2/2011 |
| JP | 2011-035116 | 2/2011 |
| JP | 2011-077486 | 4/2011 |
| JP | 2011-093848 | 5/2011 |
| JP | 2011-098906 | 5/2011 |
| JP | 2011-121886 | 6/2011 |

*Primary Examiner* — Shawquia Jackson
(74) *Attorney, Agent, or Firm* — Oblon, McClelland, Maier & Neustadt, L.L.P.

(57) ABSTRACT

A fullerene derivative having 60 or more carbon atoms, includes at least one specific structure.

8 Claims, 1 Drawing Sheet

| 6. NEGATIVE ELECTRODE |
|---|
| 5. ELECTRON TAKEOFF LAYER |
| 4. MIXED LAYER |
| 3. POSITIVE HOLE TAKEOFF LAYER |
| 2. POSITIVE ELECTRODE |
| 1. TRANSPARENT SUBSTRATE |

FULLERENE DERIVATIVE, AND METHOD OF PREPARING THE SAME

CROSS-REFERENCE TO RELATED APPLICATIONS

This patent application is based on and claims priority pursuant to 35 U.S.C. §119 to Japanese Patent Application No. 2013-255722, filed on Dec. 11, 2013, in the Japan Patent Office, the entire disclosure of which is hereby incorporated by reference herein.

BACKGROUND

1. Technical Field

The present invention relates to a new fullerene derivative useful as an organic semiconductive material and a method of preparing the same.

2. Description of the Related Art

Organic semiconductive materials are well studied in an organic electronics field such as organic transistors and organic ELs. Further, an organic solar battery using a fullerene derivative as an organic photoelectric conversion element is strenuously studied. As the most famous fullerene derivative in this field, [6,6]-phenylC61-butyric methyl ester (PCBM) which is soluble in an organic solvent is disclosed in J. Org. Chem. 1995, 60, 532-538. A functional group having a suitable size is introduced to the fullerene and solubility in an organic solvent is adjusted to increase an area of a pn bonded interface which is a charge generation area and photoelectric conversion efficiency. However, the photoelectric conversion efficiency is still insufficient, and a better fullerene derivative is required.

Japanese published unexamined applications Nos. JP-2011-26235-A, JP-2011-35116-A, JP-2011-77486-A, JP-2011-93848-A, JP-2011-98906-A and JP-2011-121886-A disclose fullerene derivatives various functional groups are introduced to for the purpose of improving an open end voltage and expanding absorption wavelength area. Bulky functional groups are introduced to the fullerenes to improve solubility in an organic solvent, and further, compatibility with a p-type semiconductive material is increased to improve photoelectric conversion efficiency. However, being short of solubility in an organic solvent, these are unable to construct a close bulk hetero junction structure in combination with the low-molecular-weight p-type semiconductive material expected to have particularly high durability, and do not have sufficiently satisfactory photoelectric conversion efficiency.

SUMMARY

Accordingly, one object of the present invention is to provide a fullerene derivative having high solubility in an organic solvent and high photoelectric conversion efficiency.

Another object of the present invention is to provide a method of producing the fullerene derivative.

These objects and other objects of the present invention, either individually or collectively, have been satisfied by the discovery of a fullerene derivative having 60 or more carbon atoms, including at least one structure having the following formula (I):

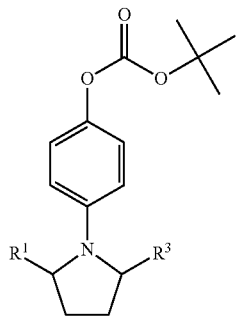

wherein $R^1$ and $R^3$ independently represent a hydrogen atom, a halogen atom, a substituted or unsubstituted alkyl group, a substituted or unsubstituted alkoxy group, a substituted or unsubstituted aryl group, a substituted or unsubstituted monofunctional heterocyclic group, or a group having the following formula (II) or (III), and at least one of $R^1$ and $R^3$ is a group having the formula (II) or (III):

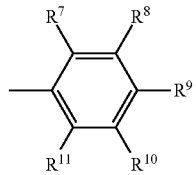

wherein $R^7$, $R^8$, $R^9$, $R^{10}$ and $R^{11}$ independently represent a hydrogen atom, a halogen atom, a substituted or unsubstituted alkyl group, a substituted or unsubstituted alkoxy group, a substituted or unsubstituted alkoxycarbonyloxy group, a substituted or unsubstituted aryl group, a substituted or unsubstituted monofunctional heterocyclic group, or a methoxy group, and at least one or more thereof are methoxy groups;

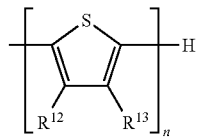

wherein $R^{12}$ and $R^{13}$ independently represent a hydrogen atom, a halogen atom, a substituted or unsubstituted alkyl group, a substituted or unsubstituted alkoxy group, a substituted or unsubstituted aryl group, or a substituted or unsubstituted monofunctional heterocyclic group; and n represents an integer of from 1 to 8.

These and other objects, features and advantages of the present invention will become apparent upon consideration of the following description of the preferred embodiments of the present invention taken in conjunction with the accompanying drawings.

BRIEF DESCRIPTION OF THE DRAWINGS

Various other objects, features and attendant advantages of the present invention will be more fully appreciated as the same becomes better understood from the detailed description when considered in connection with the accompanying drawings in which like reference characters designate like corresponding parts throughout and wherein:

FIGURE is an embodiment of configuration of an organic solar battery.

DETAILED DESCRIPTION

The present invention provides a fullerene derivative having high solubility in an organic solvent and high photoelectric conversion efficiency.

The fullerene derivative of the present invention includes one or more structure having the formula (I) together with two carbon atoms the fullerene is adjacent to:

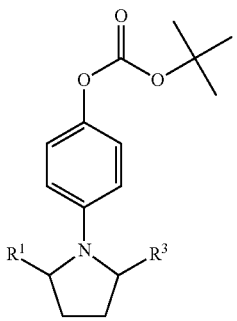

(I)

wherein $R^1$ and $R^3$ independently represent a hydrogen atom, a halogen atom, a substituted or unsubstituted alkyl group, a substituted or unsubstituted alkoxy group, a substituted or unsubstituted aryl group, a substituted or unsubstituted monofunctional heterocyclic group, or a group having the following formula (II) or (III), and at least one of $R^1$ and $R^3$ is a group having the formula (II) or (III):

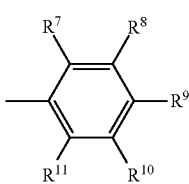

(II)

wherein $R^7$, $R^8$, $R^9$, $R^{10}$ and $R^{11}$ independently represent a hydrogen atom, a halogen atom, a substituted or unsubstituted alkyl group, a substituted or unsubstituted alkoxy group, a substituted or unsubstituted alkoxycarbonyloxy group, a substituted or unsubstituted aryl group, a substituted or unsubstituted monofunctional heterocyclic group, or a methoxy group, and at least one or more thereof are methoxy groups;

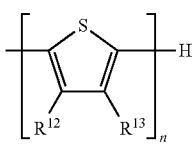

(III)

wherein $R^{12}$ and $R^{13}$ independently represent a hydrogen atom, a halogen atom, a substituted or unsubstituted alkyl group, a substituted or unsubstituted alkoxy group, a substituted or unsubstituted aryl group, or a substituted or unsubstituted monofunctional heterocyclic group; and n represents an integer of from 1 to 8.

The fullerene of the present invention includes 60 or more carbon atoms such as C60, C70, C76, C78, C80, C82, C84, C86, C88, C90, C92, C94 and C96.

The halogen atom in the formula (I) includes a fluorine atom, a chlorine atom, a bromine atom, and an iodine atom.

The substituted or unsubstituted alkyl group in the formula (I) has 1 to 30 carbon atoms, and may be straight-chain, branched-chain alkyl group or a cycloalkyl group. Specific examples of the alkyl group include methyl groups, ethyl groups, n-propyl groups, i-propyl groups, n-butyl groups, i-butyl groups, tert-butyl groups, sec-butyl groups, 3-methylbutyl groups, n-pentyl groups, n-hexyl groups, 2-ethylhexyl groups, n-heptyl groups, n-octyl groups, n-nonyl groups, n-decyl groups and n-lauryl groups. The alkyl group may have a substituent, and specific examples of the substituent include alkyl groups having 1 to 12 carbon atoms such as hydroxy groups, methyl groups, ethyl groups, tert-butyl groups and octyl groups; aryl groups having 6 to 12 carbon atoms such as phenyl groups, naphthyl groups and phenyl groups; aralkyl groups having 7 to 12 carbon atoms such as benzyl groups; acyl groups having 2 to 2 carbon atoms such as glycidyloxy groups and acetyl groups; acyloxy groups having 1 to 12 carbon atoms such as acetyloxy group; amino groups substituted with alkyl groups having 1 to 12 carbon atoms such as amino groups, methylamino groups, ethylamino groups and dimethylamino groups; halogeno groups (halogen atoms) such as fluoro groups (fluorine atoms), chloro groups (chlorine atoms) and bromo groups (bromine atoms); oxo groups (=O); and carboxy groups (—COOH).

The substituted or unsubstituted alkoxy group in the formula (I) has 1 to 30 carbon atoms, and may be straight-chain, branched-chain alkyl group or a cycloalkyl group. Specific examples of the alkoxy group include methoxy groups, ethoxy groups, n-propyloxy groups, i-propyloxy groups, n-butoxy groups, i-butoxy groups, sec-butoxy groups, tert-butoxy groups, n-pentyloxy groups, n-hexyloxy groups, cyclohexyloxy groups, n-heptyloxy groups, n-octyloxy groups, 2-ethylhexyloxy groups, n-nonyloxy groups, n-decyloxy groups, 3,7-dimethyloxyloxy groups and n-lauryloxy groups. The alkoxy group may have a substituent, and specific examples of the substituent include the same substituents of the alkyl groups.

The substituted or unsubstituted aryl group in the formula (I) has 6 to 60 carbon atoms, and specific examples thereof include phenyl groups, alkylphenyl groups, alkoxyphenyl groups, 1-naphtyl groups and 2-naphtyl groups. The aryl group may have a substituent, and specific examples of the substituent include, besides the substituents having the formula (II), the same substituents of the alkyl groups.

The substituted or unsubstituted monofunctional heterocyclic group in the formula (I) has at least one nitrogen atom, one oxygen atom or one sulfur atom in its ring, and the one ring has 5 to 20 members. Specific examples thereof include pyridyl groups, thienyl groups, phenylthienyl groups, thiazolyl groups, furyl groups, piperidyl groups, piperazyl groups, pyrrolyl groups, morpholino groups, imidazolyl groups, indolyl groups, quinolyl groups, and pyrimidinyl groups. The monofunctional heterocyclic group may have a substituent, and specific examples of the substituent include the same substituents of the alkyl groups.

At least one of $R^1$ and $R^3$ in the formula (I) is a group having the formula (II) or (III).

Specific examples of the hydrogen atom, the halogen atom, the substituted or unsubstituted alkyl group, the substituted or unsubstituted alkoxy group, the substituted or unsubstituted alkoxycarbonyloxy group, the substituted or unsubstituted aryl group, the substituted or unsubstituted monofunctional heterocyclic group, or their substituents of $R^7$, $R^8$, $R^9$, $R^{10}$, $R^{11}$, $R^{12}$ and $R^{13}$ include the same as those of $R^1$ and $R^3$.

The substituted or unsubstituted alkoxycarbonyloxy group in the formula (I) has 1 to 30 carbon atoms, and may be straight-chain, branched-chain alkyl group or a cycloalkyloxy group. Specific examples of the alkoxycarbonyloxy group include methoxycarbonyloxy groups, ethoxycarbonyloxy groups, n-propylcarbonyloxy groups, i-propylcarbonyloxy groups, n-butoxycarbonyloxy groups, i-butoxycarbonyloxy groups, sec-butoxycarbonyloxy groups, tert-butoxycarbonyloxy groups, n-pentyloxycarbonyloxy groups, n-hexyloxycarbonyloxy groups, and cyclohexyloxycarbonyloxy groups. The alkoxycarbonyloxy group may have a substituent, and specific examples of the substituent include the same substituents of the alkyl groups.

The following tables show specific structures formed in the fullerene as fullerene derivatives in the form of substituents ($R^1$, $R^2$ and $R^3$) having the following formula (VI):

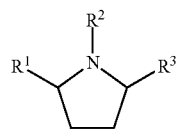

TABLE 1

| | $R^1$ | $R^2$ | $R^3$ |
|---|---|---|---|
| 1 | —H | 4-(tert-butoxycarbonyloxy)phenyl | —H |
| 2 | —H | 4-(tert-butoxycarbonyloxy)phenyl | —CH₃ |
| 3 | —H | 4-(tert-butoxycarbonyloxy)phenyl | —CH₂CH₃ |
| 4 | —H | 4-(tert-butoxycarbonyloxy)phenyl | —CH₂CH₂CH₃ |
| 5 | —H | 4-(tert-butoxycarbonyloxy)phenyl | —CH(CH₃)₂ |
| 6 | —H | 4-(tert-butoxycarbonyloxy)phenyl | —CH₂CH₂CH₂CH₃ |

TABLE 1-continued
| | R¹ | R² | R³ |
|---|---|---|---|
| 7 | —H | 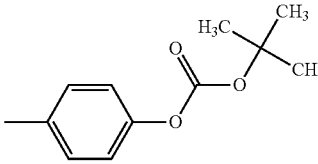 | 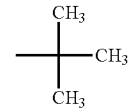 |
| 8 | —H | 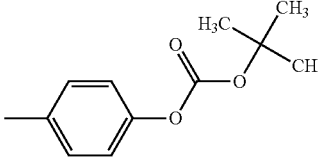 | 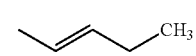 |
| 9 | —H | 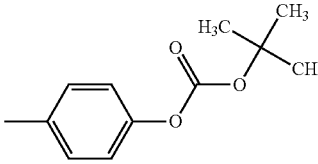 | 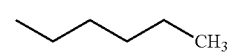 |
| 10 | —H | 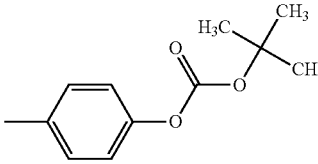 | 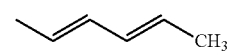 |
| 11 | —H | 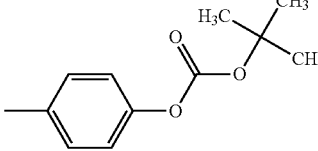 | 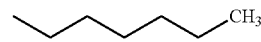 |
| 12 | —H | 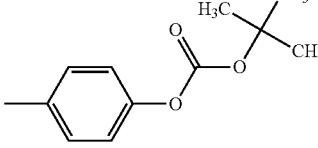 | 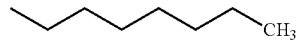 |
| 13 | —H | 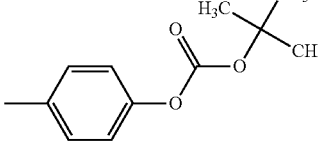 | 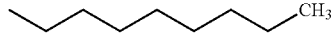 |
| 14 | —H | 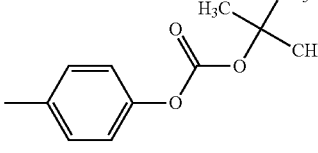 | 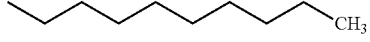 |
| 15 | —H | 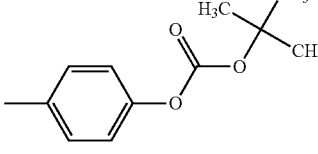 |  |

TABLE 1-continued
| | R¹ | R² | R³ |
|---|---|---|---|
| 16 | —H | 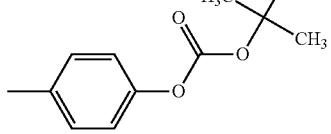 | 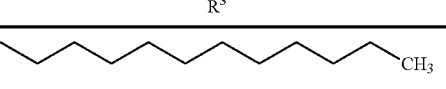 |
| 17 | —H | 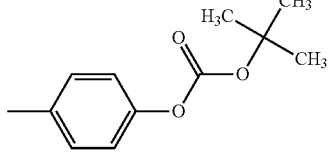 | 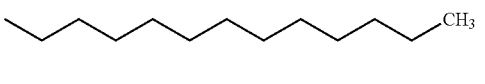 |
| 18 | —H | 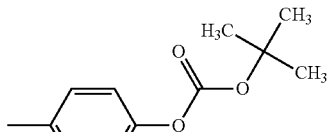 | 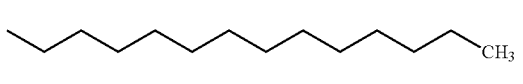 |
| 19 | —H | 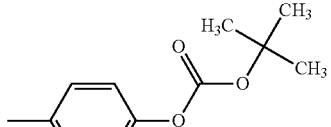 |  |
| 20 | —H | 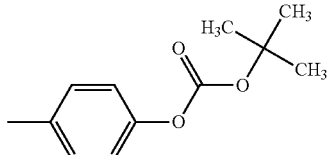 | 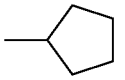 |
| 21 | —H | 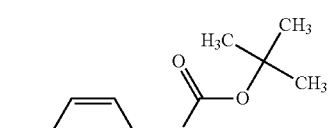 | 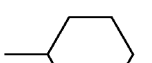 |
| 22 | —H | 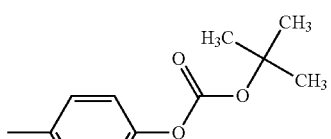 | 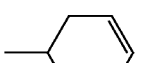 |
| 23 | —H | 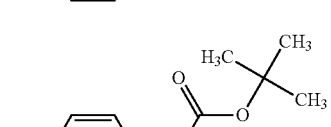 | 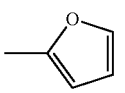 |
| 24 | —H | 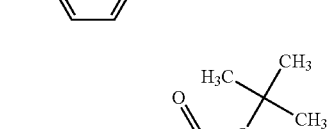 | 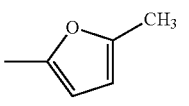 |

TABLE 1-continued

| | R¹ | R² | R³ |
|---|---|---|---|
| 25 | —H | 4-(Boc-O)-phenyl- | 5-(hydroxymethyl)furan-2-yl |
| 26 | —H | 4-(Boc-O)-phenyl- | 5-bromofuran-2-yl |
| 27 | —H | 4-(Boc-O)-phenyl- | 5-phenylfuran-2-yl |
| 28 | —H | 4-(Boc-O)-phenyl- | phenyl |
| 29 | —H | 4-(Boc-O)-phenyl- | 4-methylphenyl |
| 30 | —H | 4-(Boc-O)-phenyl- | 4-tert-butylphenyl |
| 31 | —H | 4-(Boc-O)-phenyl- | 4-fluorophenyl |
| 32 | —H | 4-(Boc-O)-phenyl- | 4-(dimethylamino)phenyl |
| 33 | —H | 4-(Boc-O)-phenyl- | 4-nitrophenyl |

TABLE 1-continued
| | R¹ | R² | R³ |
|---|---|---|---|
| 34 | —H | 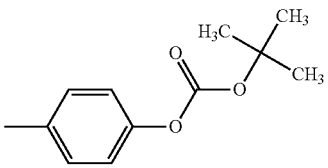 | 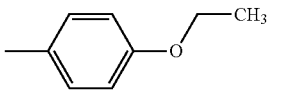 |
| 35 | —H | 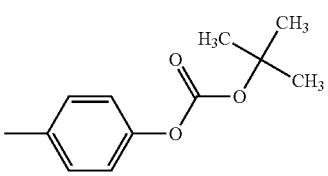 | 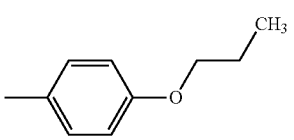 |
| 36 | —H | 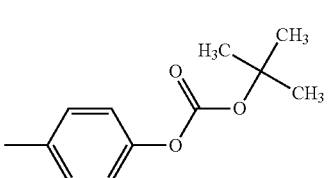 | 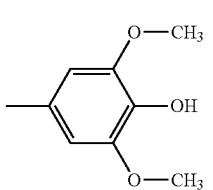 |
| 37 | —H | 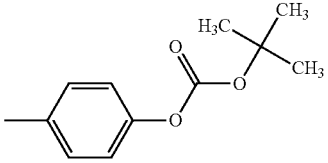 | 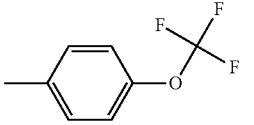 |
| 38 | —H | 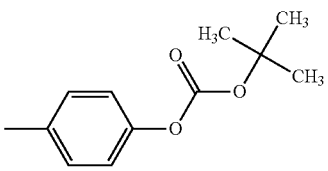 | 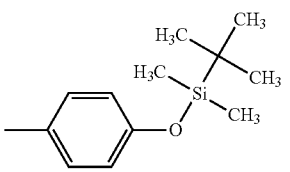 |
| 39 | —H | 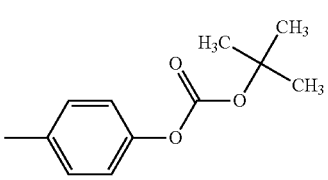 | 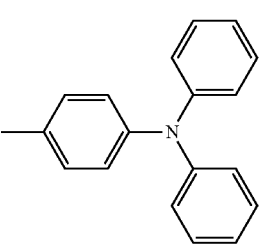 |
| 40 | —H | 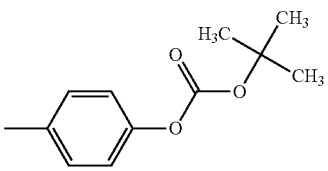 | 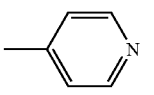 |
| 41 | —H | 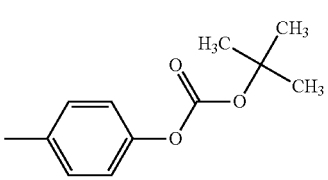 | 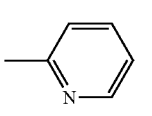 |

TABLE 1-continued
| | R¹ | R² | R³ |
|---|---|---|---|
| 42 | —H | 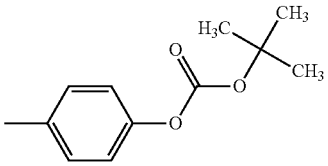 | 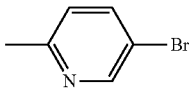 |
| 43 | —H | 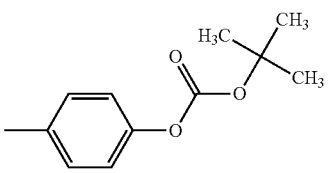 | 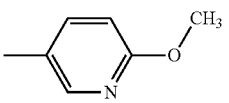 |
| 44 | —H | 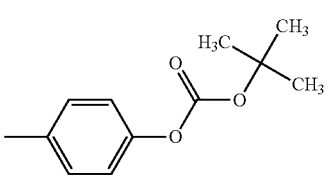 | 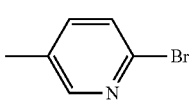 |
| 45 | —H | 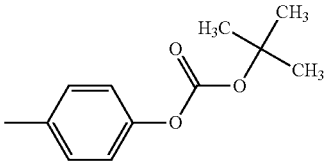 | 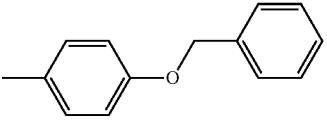 |
| 46 | —H | 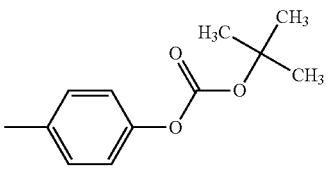 | 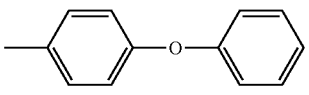 |
| 47 | —H | 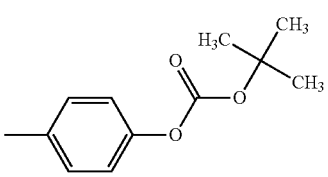 | 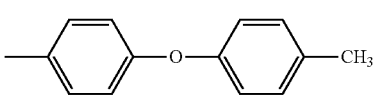 |
| 48 | —H | 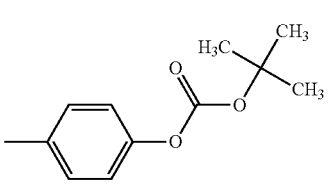 | 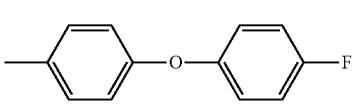 |
| 49 | —H | 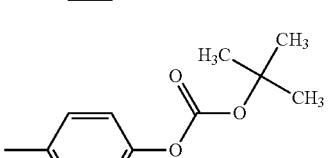 | 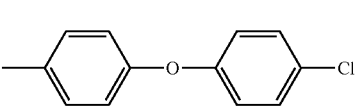 |
| 50 | —H | 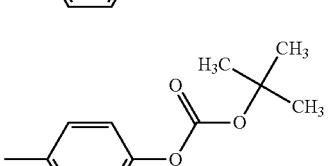 | 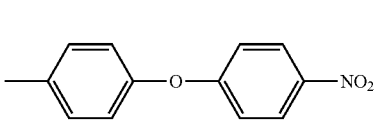 |

TABLE 1-continued
| | R¹ | R² | R³ |
|---|---|---|---|
| 51 | —H |  |  |
| 52 | —H | 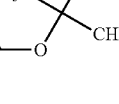 | 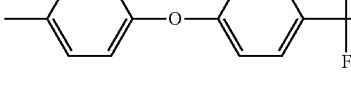 |
| 53 | —H | 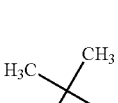 | 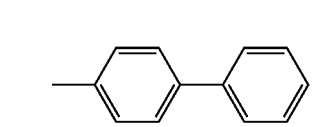 |
| 54 | —H | 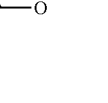 |  |
| 55 | —H | 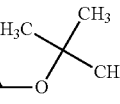 | 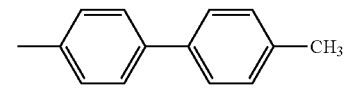 |
| 56 | —H | 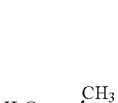 | 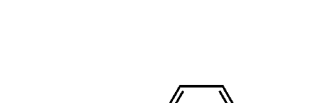 |
| 57 | —H | 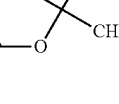 | 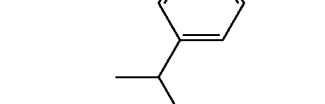 |
| 58 | —H |  | 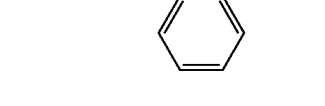 |

TABLE 1-continued

| | R¹ | R² | R³ |
|---|---|---|---|
| 59 | —H | 4-(tert-butoxycarbonyloxy)phenyl | acenaphthylenyl |
| 60 | —H | 4-(tert-butoxycarbonyloxy)phenyl | fluorenyl |
| 61 | —H | 4-(tert-butoxycarbonyloxy)phenyl | dibenzofuranyl |
| 62 | —H | 4-(tert-butoxycarbonyloxy)phenyl | anthracenyl |
| 63 | —H | 4-(tert-butoxycarbonyloxy)phenyl | phenanthrenyl |
| 64 | —H | 4-(tert-butoxycarbonyloxy)phenyl | 9-ethylcarbazolyl |
| 65 | —H | 4-(tert-butoxycarbonyloxy)phenyl | pyrenyl |

TABLE 1-continued
| | R¹ | R² | R³ |
|---|---|---|---|
| 66 | —H | 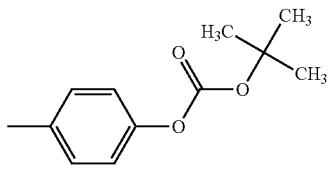 | 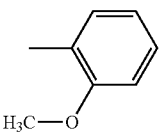 |
| 67 | —H | 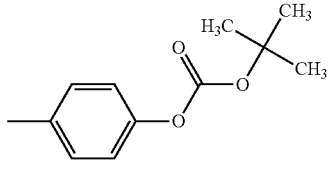 | 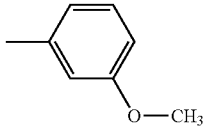 |
| 68 | —H | 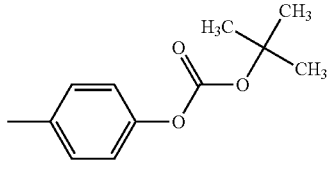 | 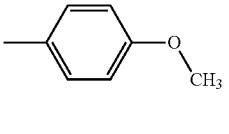 |
| 69 | —H | 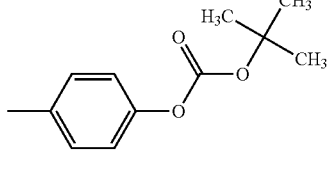 | 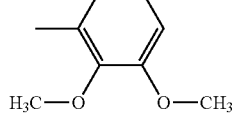 |
| 70 | —H | 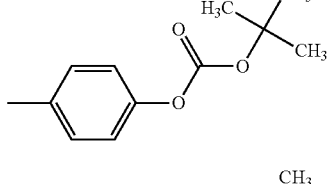 | 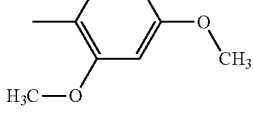 |
| 71 | —H | 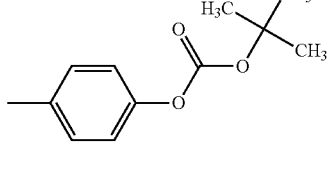 | 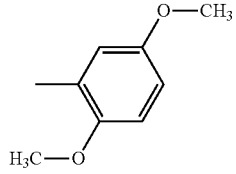 |
| 72 | —H | 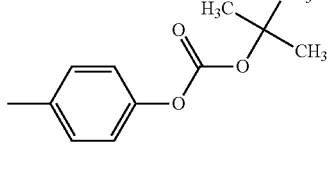 | 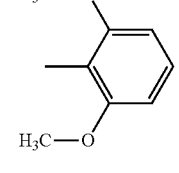 |
| 73 | —H | 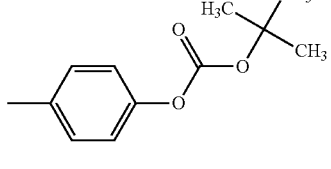 | 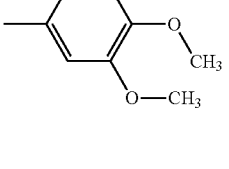 |
| 74 | —H | 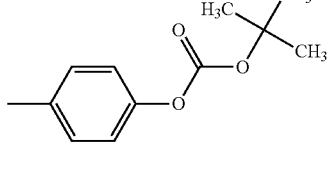 | 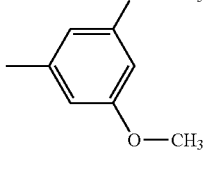 |

TABLE 1-continued

| | R¹ | R² | R³ |
|---|---|---|---|
| 75 | —H | 4-(tert-butoxycarbonyloxy)phenyl | 2,3,4-trimethoxy-6-methylphenyl |
| 76 | —H | 4-(tert-butoxycarbonyloxy)phenyl | 3,4,5-trimethoxyphenyl (methyl substituted) |
| 77 | —H | 4-(tert-butoxycarbonyloxy)phenyl | 2,3,6-trimethoxy-methylphenyl |
| 78 | —H | 4-(tert-butoxycarbonyloxy)phenyl | 2,4,5-trimethoxyphenyl (methyl substituted) |
| 79 | —H | 4-(tert-butoxycarbonyloxy)phenyl | 3,4,5-trimethoxy-methylphenyl |
| 80 | —H | 4-(tert-butoxycarbonyloxy)phenyl | 2,3,6-trimethoxyphenyl (methyl substituted) |
| 81 | —H | 4-(tert-butoxycarbonyloxy)phenyl | 2,3,4,5-tetramethoxyphenyl (methyl substituted) |
| 82 | —H | 4-(tert-butoxycarbonyloxy)phenyl | 2,3,4,5-tetramethoxyphenyl (methyl substituted) |

TABLE 1-continued
| | R¹ | R² | R³ |
|---|---|---|---|
| 83 | —H | 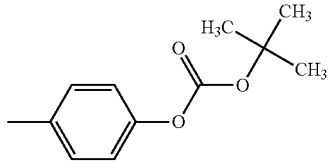 | 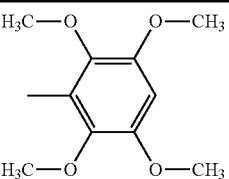 |
| 84 | —H | 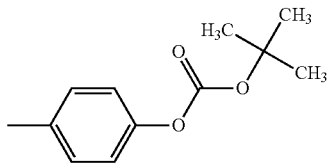 | 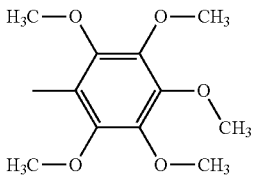 |
| 85 | —H | 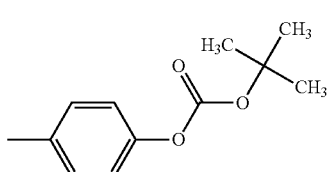 | 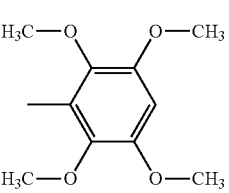 |
| 86 | —H | 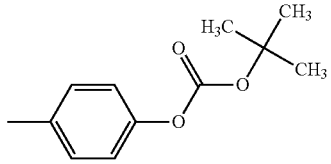 | 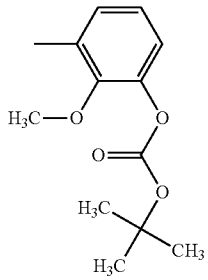 |
| 87 | —H | 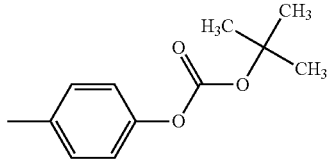 | 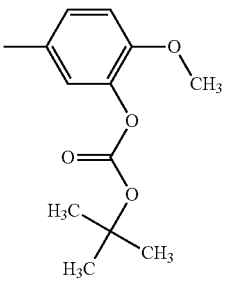 |
| 88 | —H | 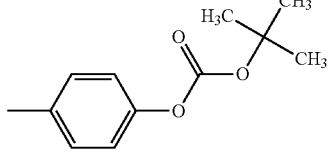 | 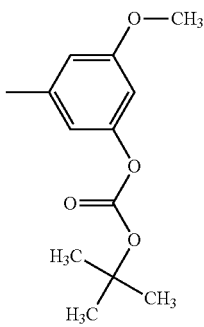 |

TABLE 1-continued
| | R¹ | R² | R³ |
|---|---|---|---|
| 89 | —H |  | 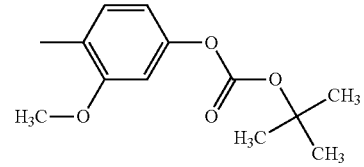 |
| 90 | —H |  | 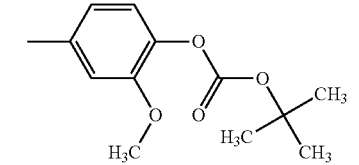 |
| 91 | —H |  | 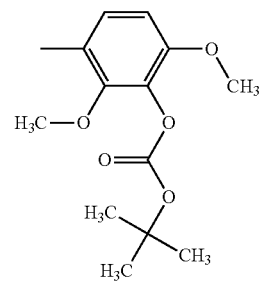 |
| 92 | —H |  | 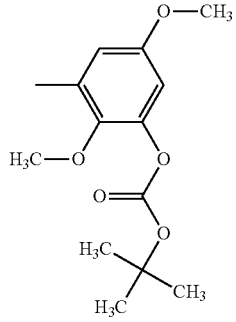 |
| 93 | —H |  | 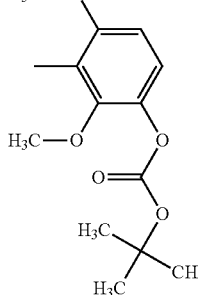 |

TABLE 1-continued

| | R¹ | R² | R³ |
|---|---|---|---|
| 94 | —H | 4-(tert-butoxycarbonyloxy)phenyl | 4,5-dimethoxy-2-(tert-butoxycarbonyloxy)phenyl (methyl substituent) |
| 95 | —H | 4-(tert-butoxycarbonyloxy)phenyl | 2,5-dimethoxy-4-(tert-butoxycarbonyloxy)phenyl (methyl substituent) |
| 96 | —H | 4-(tert-butoxycarbonyloxy)phenyl | 2,3-dimethoxy-4-methyl-6-(tert-butoxycarbonyloxy)phenyl |
| 97 | —H | 4-(tert-butoxycarbonyloxy)phenyl | 2,5-dimethoxy-4-methyl-(tert-butoxycarbonyloxy)phenyl |
| 98 | —H | 4-(tert-butoxycarbonyloxy)phenyl | 3,5-dimethoxy-4-methyl-(tert-butoxycarbonyloxy)phenyl |
| 99 | —H | 4-(tert-butoxycarbonyloxy)phenyl | 2,6-dimethoxy-4-methyl-(tert-butoxycarbonyloxy)phenyl |

TABLE 1-continued
| | R¹ | R² | R³ |
|---|---|---|---|
| 100 | —H | 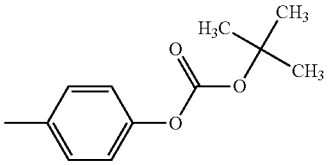 | 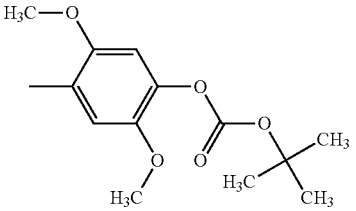 |
| 101 | —H | 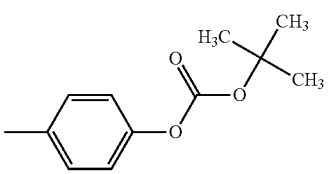 | 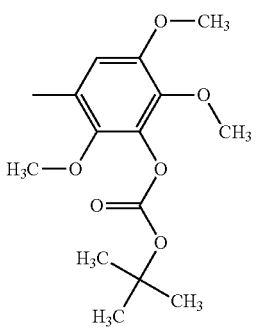 |
| 102 | —H | 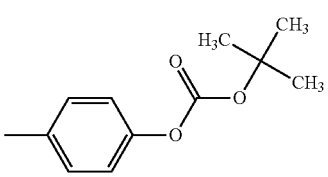 | 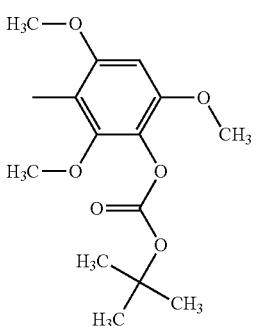 |
| 103 | —H | 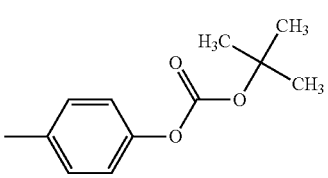 | 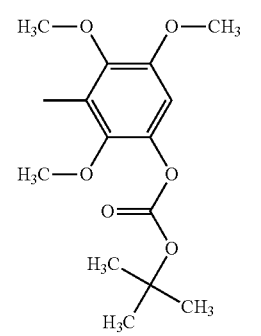 |
| 104 | —H | 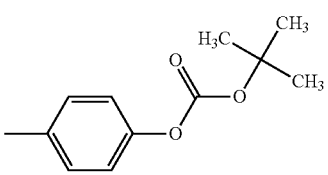 | 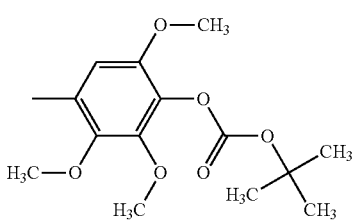 |

TABLE 1-continued
| | R¹ | R² | R³ |
|---|---|---|---|
| 105 | —H | 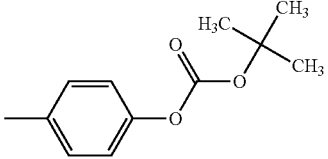 | 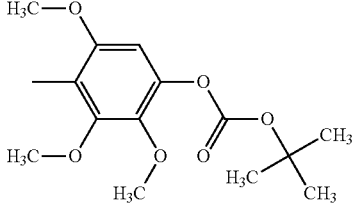 |
| 106 | —H | 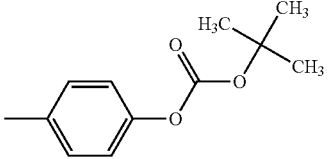 | 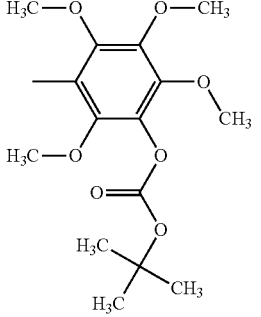 |
| 107 | —H | 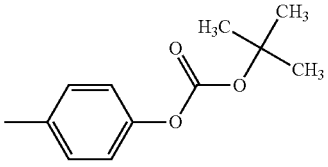 | 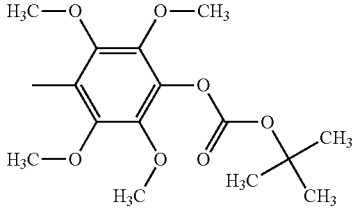 |
| 108 | —H | 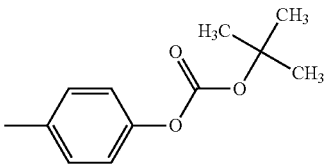 | 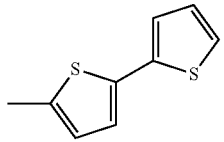 |
| 109 | —H | 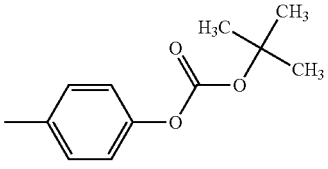 | 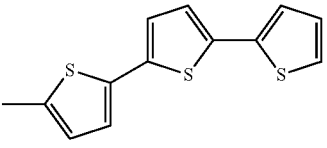 |
| 110 | —H | 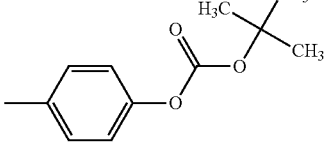 | 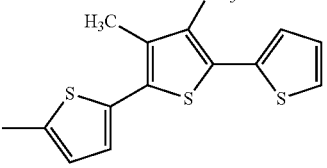 |
| 111 | —H | 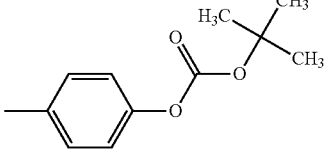 | 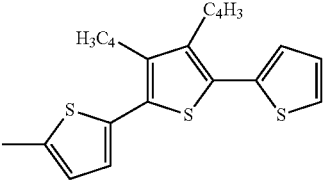 |

TABLE 1-continued
| | R¹ | R² | R³ |
|---|---|---|---|
| 112 | —H |  | 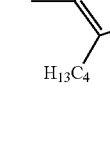 |
| 113 | —H | 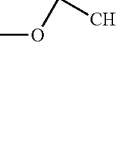 | 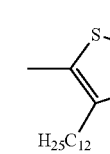 |
| 114 | —H | 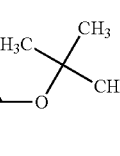 | 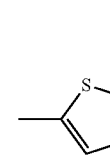 |
| 115 | —H | 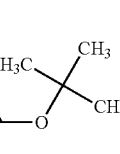 | 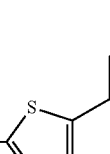 |
| 116 | —H | 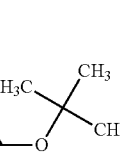 | 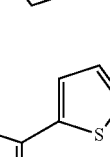 |
| 117 | —H | 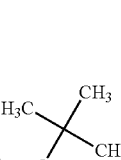 | 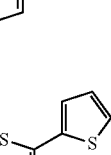 |
| 118 | —H | 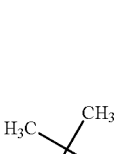 |  |
| 119 | —H | —CH₃ | 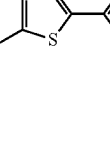 |

TABLE 1-continued

| | R¹ | R² | R³ |
|---|---|---|---|
| 120 | —H | —CH₃ | 4-methylphenyl tert-butyl carbonate |
| 121 | —H | —CH₃ | 2,6-dimethoxy-4-methylphenyl tert-butyl carbonate |
| 122 | —H | —CH₃ | 2-methoxy-3-methylphenyl tert-butyl carbonate |
| 123 | —H | —CH₃ | 3-methoxy-4-methylphenyl tert-butyl carbonate |
| 124 | —H | —CH₃ | 2,4-dimethoxy-3-methylphenyl tert-butyl carbonate |
| 125 | —H | phenyl | 3-methylphenyl tert-butyl carbonate |
| 126 | —H | phenyl | 4-methylphenyl tert-butyl carbonate |

TABLE 1-continued

| | R¹ | R² | R³ |
|---|---|---|---|
| 127 | —H | 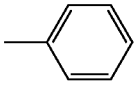 | 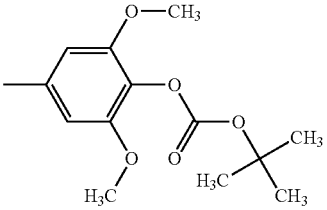 |
| 128 | —H | 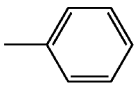 | 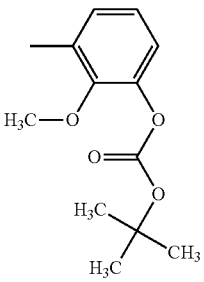 |
| 129 | —H | 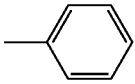 | 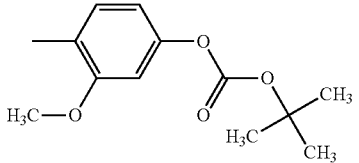 |
| 130 | —H | 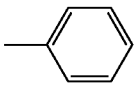 | 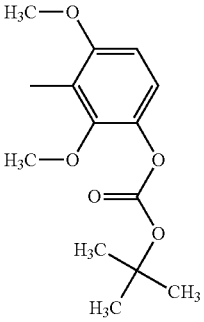 |

Examples 66 to 118 are included in the present invention.

The fullerene derivative includes at least one structure having the formula (I), and may one 2 to 4 structures. Relative positions of the plural structures are not limited.

A precursor of the fullerene derivative of the present invention is synthesized by reacting a glycin derivative with an aldehyde derivative to produce azomethine ylide; adding the azomethine ylide to fullerene through Prato reaction (J. Am. Chem. SOC. 1993, 115, 9787-9799).

Specific examples of the glycin derivative include a glycin derivative having the following formula (VII):

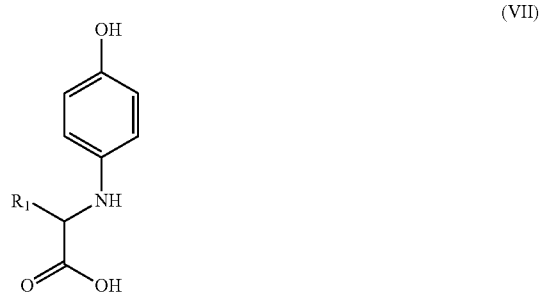

(VII)

wherein $R^1$ represents a hydrogen atom, a halogen atom, a substituted or unsubstituted alkyl group, a substituted or unsubstituted alkoxy group, a substituted or unsubstituted aryl group, a substituted or unsubstituted monofunctional heterocyclic group, or a group having the following formula (II) or (III):

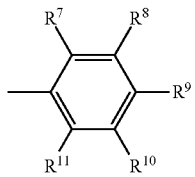

(II)

wherein $R^7$, $R^8$, $R^9$, $R^{10}$ and $R^{11}$ independently represent a hydrogen atom, a halogen atom, a substituted or unsubstituted alkyl group, a substituted or unsubstituted alkoxy group, a substituted or unsubstituted alkoxycarbonyloxy group, a substituted or unsubstituted aryl group, a substituted or unsubstituted monofunctional heterocyclic group, or a methoxy group, and at least one or more thereof are methoxy groups;

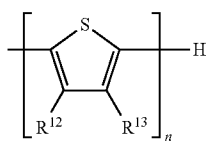

(III)

wherein $R^{12}$ and $R^{13}$ independently represent a hydrogen atom, a halogen atom, a substituted or unsubstituted alkyl group, a substituted or unsubstituted alkoxy group, a substituted or unsubstituted aryl group, or a substituted or unsubstituted monofunctional heterocyclic group; and n represents an integer of from 1 to 8.

An amount of the glycin derivative used is preferably from 0.1 to 10 mol, and more preferably from 0.5 to 5 mol per 1 mol of fullerene.

Specific examples of the aldehyde derivative include a aldehyde derivative having the following formula (VIII):

 $R^3$—CHO       (VIII)

wherein $R^3$ represents a hydrogen atom, a halogen atom, a substituted or unsubstituted alkyl group, a substituted or unsubstituted aryl group, a substituted or unsubstituted monofunctional heterocyclic group, or a group having the following formula (II) or (III):

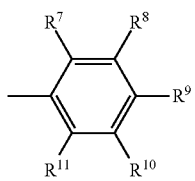

(II)

wherein $R^7$, $R^8$, $R^9$, $R^{10}$ and $R^{11}$ independently represent a hydrogen atom, a halogen atom, a substituted or unsubstituted alkyl group, a substituted or unsubstituted alkoxy group, a substituted or unsubstituted alkoxycarbonyloxy group, a substituted or unsubstituted aryl group, a substituted or unsubstituted monofunctional heterocyclic group, or a methoxy group, and at least one or more thereof are methoxy groups;

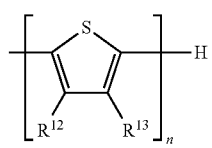

(III)

wherein $R^{12}$ and $R^{13}$ independently represent a hydrogen atom, a halogen atom, a substituted or unsubstituted alkyl group, a substituted or unsubstituted alkoxy group, a substituted or unsubstituted aryl group, or a substituted or unsubstituted monofunctional heterocyclic group; and n represents an integer of from 1 to 8.

The substituents of $R^1$ in the formula (VII) and $R^3$ in the formula (VIII) are the same as those in the formulae (II) and (III).

At least one of $R^1$ in the formula (VII) and $R^3$ in the formula (VIII) has the substituents in the formulae (II) or (III).

An amount of the aldehyde derivative used is preferably from 0.1 to 10 mol, and more preferably from 0.5 to 5 mol per 1 mol of fullerene.

In the Prato reaction, an organic solvent can be used. Specific examples thereof include toluene, benzene, hexane, cyclohexane, octane, xylene, chlorobenzene, carbon tetrachloride, 1-chloronaphthalene, etc. An amount of the organic solvent used is preferably from 1 to 100,000 times of the weight of fullerene.

Specific examples of the method of synthesizing the fullerene derivative include mixing fullerene, a glycin derivative and an aldehyde derivative, and heating them in an organic solvent at 50 to 350° C. for 30 min to 50 hrs. After heated, the reactant mixture is cooled to have room temperature, and the solvent is removed by a rotary evaporator under reduced pressure. Further, the resultant solid is separated and refined by silica gel flash column chromatography to prepare fullero pyrrolidine having the following formula (IV) which is a precursor of the fullerene derivative:

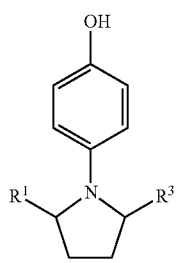

(IV)

wherein $R^1$ and $R^3$ independently represent a hydrogen atom, a halogen atom, a substituted or unsubstituted alkyl group, a substituted or unsubstituted alkoxy group, a substituted or unsubstituted aryl group, a substituted or unsubstituted monofunctional heterocyclic group, or a group having the formula (II) or (III), and at least one of $R^1$ and $R^3$ is a group having the formula (II) or (III).

Next, the fullero pyrrolidine derivative is reacted with diesterpyrocarbonate having the following formula (V) in a non-proton organic solvent under the presence of a base as a catalyst as disclosed in Japanese published unexamined application No. JP-2009-7523-A to prepare an embodiment of the fullerene derivative having the formula (I) of the present invention.

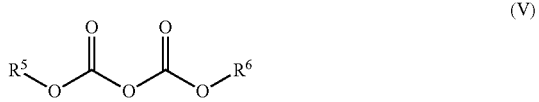

(V)

wherein $R^5$ and $R^6$ represent a tert-butyl group.

Specific examples of the non-proton organic solvent include ether solvents such as tetrahydrofuran and dioxane, glycol ether solvents such as ethyleneglycolmethylether and ethyleneglycolethylether, acetonitrile, N,N-dimethylformaldehyde, N,N-dimethylacetoamide, ethylcellosolve, ethylacetate, methylacetate, dichloromethane, monochlorobenzene, toluene, xylene, nitrobenzene, pyridine, picoline, quinoline, etc. The organic solvents used in the Prato reaction can also be used. An amount of the non-proton organic solvent used is preferably from 1 to 100,000 times of the weight of fullerene.

The base used as a catalyst includes alkali metals, and their hydrides and carbonates such as sodium and potassium; alkali metal amides such as sodium amides and potassium amides; and hydrogenated alkali metals such as hydrogenated lithium. As organic aliphatic bases, aromatic bases and heterocyclic N-bases, diazabicyclooctene, diazabicycloundecene, 4-dimethylaminopyridine, dimethylpyridine, pyridine, triethylamine, etc. An amount of the base used is preferably from 0.01 to 10 mol, and more preferably from 0.5 to 1 mol per 1 mol of fullerene.

The diesterpyrocarbonate having the formula (V) can be prepared by known methods, and is commercially available. An amount of the diesterpyrocarbonate having the formula (V) used is preferably from 0.1 to 20 mol, and more preferably from 0.5 to 10 mol per 1 mol of fullerene.

The fullerene derivative of the present invention has high solubility in an organic solvent and is capable of forming a close domain structure even in a combination with a low-molecular-weight p-type semiconductive material, which has been unrealizable with the conventional fullerene derivative. As a result, the fullerene derivative is effectively used in an organic electronics field where the domain structure thereof has an important role. Specifically, the fullerene derivative is dissolved in an organic solvent to prepare a solution, and the solution is coated as a coating liquid.

The fullerene derivative of the present invention can be used as an organic semiconductive material for organic transistors, organic ELs, organic solar batteries, etc. Organic semiconductive devices obtained from the fullerene derivative of the present invention can be prepared according to methods known in technical fields they belong to.

Particularly, the fullerene derivative of the present invention is a promising organic semiconductive material for the organic solar batteries, and an embodiment thereof is explained.

FIGURE is an embodiment of configuration of an organic solar battery. The organic solar battery is formed by the following method. A positive electrode of, e.g., an electroconductive metal material is formed on a transparent substrate such as glasses. The positive electrode is formed by vacuum vapor deposition methods, etc. Next, a positive hole takeout layer is formed on the positive electrode when necessary. The positive hole takeout layer is formed by coating methods, etc., using a p-type semiconductive material. The positive hole takeout layer is preferably subjected to an annealing treatment exposing the layer to a solvent vapor under a solvent atmosphere or an annealing treatment heating the layer when necessary. A mixed layer formed of a p-type semiconductive material and an n-type semiconductive material, including at least the fullerene derivative of the present invention is formed on the positive hole takeout layer. The mixed layer is formed by coating. The mixed layer is preferably subjected to an annealing treatment with a solvent or heat as well. The fullerene derivative of the present invention is capable of releasing the functional group having the formula (II) when heated to reduce solubility. Therefore, the annealing treatment with heat is preferably used. The heating temperature is preferably from 50 to 300° C., and the heating time is preferably from 1 min to 20 hrs. When the annealing treatment with heat positively reduces solubility of the fullerene derivative, the size of the domain thereof can be controlled. Therefore, a fine p/n bonded interface unformable with conventional fullerene derivatives can be formed to realize high incident photon-to-current conversion efficiency. Next, an electron takeout layer is formed on the mixed layer. The electron takeout layer is formed by dry or wet film forming methods with an n-type semiconductive material. The electron takeout layer is preferably subjected to the annealing treatment with a solvent or a heat as well. The positive hole takeout layer and the electron takeout layer are formed when necessary, and may not be formed. Next, a negative electrode is formed on the electron takeout layer. The negative electrode is formed by vacuum vapor deposition methods, etc. as the positive electrode is.

EXAMPLES

Having generally described this invention, further understanding can be obtained by reference to certain specific examples which are provided herein for the purpose of illustration only and are not intended to be limiting. In the descriptions in the following examples, the numbers represent weight ratios in parts, unless otherwise specified.

Example 1

(Synthesis Example of Fullerene Derivative Having One Structure 66)
[Step 1] Synthesis of Fullero Pyrrolidine
Fullerene $C_{60}$ (250 mg, 0.35 mmol), N-(4-hydroxyphenyl) glycin (585 mg, 3.50 mmol), 2-methoxybenzaldehyde (238 mg, 1.75 mmol) and chlorobenzene (100 mL) were placed in a 200-mL double-necked flask equipped with Gimroth condenser, and heated to reflux for 3 hrs. After the mixture was cooled to have a room temperature, the solvent was removed therefrom by a rotary evaporator. Further, after the product was separated off by silica gel column chromatography with a mixed solvent in which toluene and ethylacetate are mixed at a ratio of 10 to 1 by volume, the solvent was removed therefrom by a rotary evaporator to obtain a brown solid (100 mg).

The brown solid was subjected to IR absorption spectrum measurement, LC-MS and element analysis. The results were as follows.
IR Absorption Spectrum Measurement (KBr Tablet Method)
An absorption of OH stretching oscillation was observed at 3,440 $cm^{-1}$
LC-MS (Developing Solvent: Toluene)
m/z=961 (theoretical value: 961.93)
Element Analysis
C=93.4% (theoretical value: 93.65%)
H=1.4% (theoretical value: 1.57%)
N=1.4% (theoretical value: 1.46%)
From the above, the brown solid was found to be fullero pyrrolidine having the following formula (6) (yield rate 30.1%).

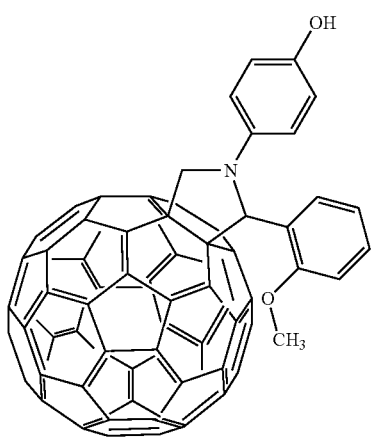

(6)

[Step 2] Synthesis of Fullerene Derivative Having One Structure 66

The fullero pyrrolidine (100 mg, 0.10 mmol), di-tert-butyl dicarbonate (227 mg, 1.04 mmol), 4-dimethylaminopyridine (127 mg, 1.04 mmol) and toluene (100 mL) were placed in a 200-mL double-necked flask equipped with Gimroth condenser, and stirred for 3 hrs at room temperature (25° C.). After the mixture was stirred, the solvent was removed therefrom by a rotary evaporator. Further, after the product was separated off by silica gel column chromatography with toluene as a solvent, the solvent was removed therefrom by a rotary evaporator to obtain a brown solid (102 mg).

The brown solid was subjected to IR absorption spectrum measurement, LC-MS and element analysis. The results were as follows.

IR Absorption Spectrum Measurement (KBr Tablet Method)

The absorption of OH stretching oscillation was observed at 3,440 cm$^{-1}$ disappeared, an absorption of C—H stretching oscillation and an absorption of C=O stretching oscillation were observed at 2,920 cm$^{-1}$ and 1,750 cm$^{-1}$, respectively.

LC-MS (Developing Solvent: Toluene)

m/z=1061 (theoretical value: 1032.04)

Element Analysis

C=90.4% (theoretical value: 90.47%)
H=2.1% (theoretical value: 2.18%)
N=1.2% (theoretical value: 1.32%)

From the above, the brown solid was found to be a fullerene derivative having one structure 66 (yield rate 92.3%).

Example 2

(Synthesis Example of Fullerene Derivative Having One Structure 73)

[Step 1] Synthesis of Fullero Pyrrolidine

Fullerene $C_{60}$ (250 mg, 0.35 mmol), N-(4-hydroxyphenyl) glycin (585 mg, 3.50 mmol), 3,4-dimethoxybenzaldehyde (291 mg, 1.75 mmol) and chlorobenzene (100 mL) were placed in a 200-mL double-necked flask equipped with Gimroth condenser, and heated to reflux for 3 hrs. After the mixture was cooled to have a room temperature, the solvent was removed therefrom by a rotary evaporator. Further, after the product was separated off by silica gel column chromatography with a mixed solvent in which toluene and ethylacetate are mixed at a ratio of 10 to 1 by volume, the solvent was removed therefrom by a rotary evaporator to obtain a brown solid (110 mg).

The brown solid was subjected to IR absorption spectrum measurement, LC-MS and element analysis. The results were as follows.

IR Absorption Spectrum Measurement (KBr Tablet Method)

An absorption of OH stretching oscillation was observed at 3,440 cm$^{-1}$

LC-MS (Developing Solvent: Toluene)

m/z=991 (theoretical value: 991.95)

Element Analysis

C=92.1% (theoretical value: 92.02%)
H=1.6% (theoretical value: 1.73%)
N=1.5% (theoretical value: 1.41%)

From the above, the brown solid was found to be fullero pyrrolidine having the following formula (7) (yield rate 32.0%).

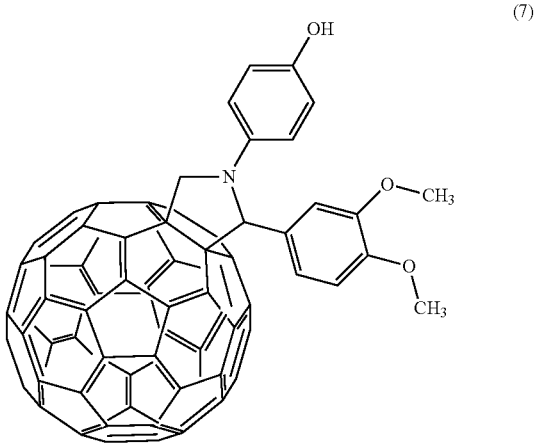

(7)

[Step 2] Synthesis of Fullerene Derivative Having One Structure 73

The fullero pyrrolidine (100 mg, 0.10 mmol), di-tert-butyl dicarbonate (220 mg, 1.01 mmol), 4-dimethylaminopyridine (123 mg, 1.01 mmol) and toluene (100 mL) were placed in a 200-mL double-necked flask equipped with Gimroth condenser, and stirred for 3 hrs at room temperature (25° C.). After the mixture was stirred, the solvent was removed therefrom by a rotary evaporator. Further, after the product was separated off by silica gel column chromatography with toluene as a solvent, the solvent was removed therefrom by a rotary evaporator to obtain a brown solid (103 mg).

The brown solid was subjected to IR absorption spectrum measurement, LC-MS and element analysis. The results were as follows.

IR Absorption Spectrum Measurement (KBr Tablet Method)

The absorption of OH stretching oscillation was observed at 3,440 cm$^{-1}$ disappeared, an absorption of C—H stretching oscillation and an absorption of C=O stretching oscillation were observed at 2,920 cm$^{-1}$ and 1,750 cm$^{-1}$, respectively.

LC-MS (Developing Solvent: Toluene)

m/z=1091 (theoretical value: 1092.07)

Element Analysis

C=89.0% (theoretical value: 89.08%)
H=2.2% (theoretical value: 2.31%)
N=1.2% (theoretical value: 1.28%)

From the above, the brown solid was found to be a fullerene derivative having one structure 73 (yield rate 93.1%).

Example 3

(Synthesis Example of Fullerene Derivative Having One Structure 99)

[Step 1] Synthesis of Fullero Pyrrolidine

Fullerene $C_{60}$ (250 mg, 0.35 mmol), N-(4-hydroxyphenyl) glycin (585 mg, 3.50 mmol), syringaldehyde (319 mg, 1.75 mmol) and chlorobenzene (100 mL) were placed in a 200-mL double-necked flask equipped with Gimroth condenser, and heated to reflux for 3 hrs. After the mixture was cooled to have a room temperature, the solvent was removed therefrom by a rotary evaporator. Further, after the product was separated off by silica gel column chromatography with a mixed solvent in which toluene and ethylacetate are mixed at a ratio of 10 to 1 by volume, the solvent was removed therefrom by a rotary evaporator to obtain a brown solid (104 mg).

The brown solid was subjected to IR absorption spectrum measurement, LC-MS and element analysis. The results were as follows.

IR Absorption Spectrum Measurement (KBr Tablet Method)
An absorption of OH stretching oscillation was observed at 3,440 cm$^{-1}$ LC-MS (Developing Solvent: Toluene)
m/z=1007 (theoretical value: 1007.95)

Element Analysis
C=90.4% (theoretical value: 90.56%)
H=1.7% (theoretical value: 1.70%)
N=1.3% (theoretical value: 1.39%)

From the above, the brown solid was found to be fullero pyrrolidine having the following formula (8) (yield rate 29.8%).

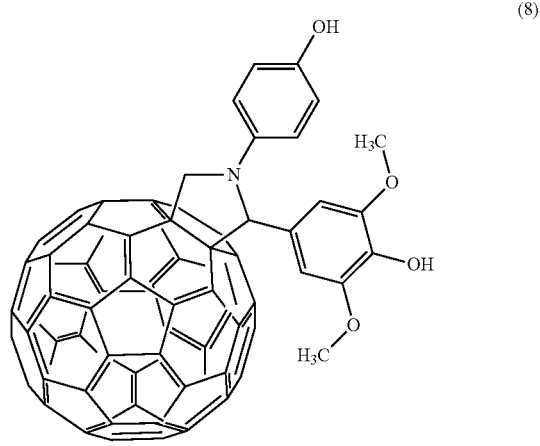

(8)

[Step 2] Synthesis of Fullerene Derivative Having One Structure 99

The fullero pyrrolidine (100 mg, 0.10 mmol), di-tert-butyl dicarbonate (217 mg, 0.99 mmol), 4-dimethylaminopyridine (121 mg, 0.99 mmol) and toluene (100 mL) were placed in a 200-mL double-necked flask equipped with Gimroth condenser, and stirred for 3 hrs at room temperature (25° C.). After the mixture was stirred, the solvent was removed therefrom by a rotary evaporator. Further, after the product was separated off by silica gel column chromatography with toluene as a solvent, the solvent was removed therefrom by a rotary evaporator to obtain a brown solid (111 mg).

The brown solid was subjected to IR absorption spectrum measurement, LC-MS and element analysis. The results were as follows.

IR Absorption Spectrum Measurement (KBr Tablet Method)
The absorption of OH stretching oscillation was observed at 3,440 cm$^{-1}$ disappeared, an absorption of C—H stretching oscillation and an absorption of C=O stretching oscillation were observed at 2,920 cm$^{-1}$ and 1,750 cm$^{-1}$, respectively.

LC-MS (Developing Solvent: Toluene)
m/z=1207 (theoretical value: 1208.18)

Element Analysis
C=85.5% (theoretical value: 85.49%)
H=2.8% (theoretical value: 2.75%)
N=1.2% (theoretical value: 1.16%)

From the above, the brown solid was found to be a fullerene derivative having one structure 99 (yield rate 92.6%).

Example 4

(Synthesis Example of Fullerene Derivative Having One Structure 56)

[Step 1] Synthesis of Fullero Pyrrolidine
Fullerene $C_{60}$ (250 mg, 0.35 mmol), N-(4-hydroxyphenyl) glycin (585 mg, 3.50 mmol), 2-thiophenecarboxyaldehyde (196 mg, 1.75 mmol) and chlorobenzene (100 mL) were placed in a 200-mL double-necked flask equipped with Gimroth condenser, and heated to reflux for 3 hrs. After the mixture was cooled to have a room temperature, the solvent was removed therefrom by a rotary evaporator. Further, after the product was separated off by silica gel column chromatography with a mixed solvent in which toluene and ethylacetate are mixed at a ratio of 10 to 1 by volume, the solvent was removed therefrom by a rotary evaporator to obtain a brown solid (113 mg).

The brown solid was subjected to IR absorption spectrum measurement, LC-MS and element analysis. The results were as follows.

IR Absorption Spectrum Measurement (KBr Tablet Method)
An absorption of OH stretching oscillation was observed at 3,440 cm$^{-1}$ LC-MS (Developing Solvent: Toluene)
m/z=937 (theoretical value: 937.93)

Element Analysis
C=92.1% (theoretical value: 92.20%)
H=1.1% (theoretical value: 1.18%)
N=1.3% (theoretical value: 1.49%)

From the above, the brown solid was found to be fullero pyrrolidine having the following formula (9) (yield rate 34.8%).

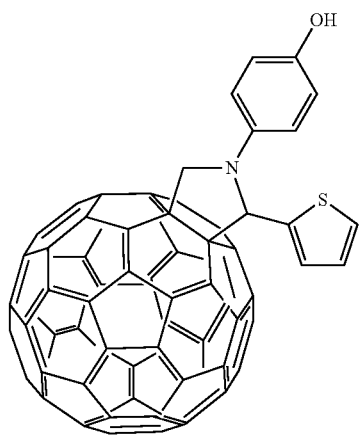

(9)

[Step 2] Synthesis of Fullerene Derivative Having One Structure 56

The fullero pyrrolidine (100 mg, 0.10 mmol), di-tert-butyl dicarbonate (233 mg, 1.07 mmol), 4-dimethylaminopyridine (130 mg, 1.07 mmol) and toluene (100 mL) were placed in a 200-mL double-necked flask equipped with Gimroth condenser, and stirred for 3 hrs at room temperature (25° C.). After the mixture was stirred, the solvent was removed therefrom by a rotary evaporator. Further, after the product was separated off by silica gel column chromatography with toluene as a solvent, the solvent was removed therefrom by a rotary evaporator to obtain a brown solid (105 mg).

The brown solid was subjected to IR absorption spectrum measurement, LC-MS and element analysis. The results were as follows.

IR Absorption Spectrum Measurement (KBr Tablet Method)

The absorption of OH stretching oscillation was observed at 3,440 cm$^{-1}$ disappeared, an absorption of C—H stretching oscillation and an absorption of C=O stretching oscillation were observed at 2,920 cm$^{-1}$ and 1,750 cm$^{-1}$, respectively.

LC-MS (Developing Solvent: Toluene)

m/z=1037 (theoretical value: 1038.04)

Element Analysis

C=89.1% (theoretical value: 89.09%)

H=1.9% (theoretical value: 1.84%)

N=1.3% (theoretical value: 1.35%)

From the above, the brown solid was found to be a fullerene derivative having one structure 56 (yield rate 94.4%).

Example 5

(Synthesis Example of Fullerene Derivative Having One Structure 108)

[Step 1] Synthesis of Fullero Pyrrolidine

Fullerene $C_{60}$ (250 mg, 0.35 mmol), N-(4-hydroxyphenyl) glycin (585 mg, 3.50 mmol), 2,2'-bithiophene-5-carboxyaldehyde (340 mg, 1.75 mmol) and chlorobenzene (100 mL) were placed in a 200-mL double-necked flask equipped with Gimroth condenser, and heated to reflux for 3 hrs. After the mixture was cooled to have a room temperature, the solvent was removed therefrom by a rotary evaporator. Further, after the product was separated off by silica gel column chromatography with a mixed solvent in which toluene and ethylacetate are mixed at a ratio of 10 to 1 by volume, the solvent was removed therefrom by a rotary evaporator to obtain a brown solid (112 mg).

The brown solid was subjected to IR absorption spectrum measurement, LC-MS and element analysis. The results were as follows.

IR Absorption Spectrum Measurement (KBr Tablet Method)

An absorption of OH stretching oscillation was observed at 3,440 cm$^{-1}$

LC-MS (Developing Solvent: Toluene)

m/z=1019 (theoretical value: 1020.05)

Element Analysis

C=89.6% (theoretical value: 89.49%)

H=1.3% (theoretical value: 1.28%)

N=1.2% (theoretical value: 1.37%)

From the above, the brown solid was found to be fullero pyrrolidine having the following formula (10) (yield rate 31.6%).

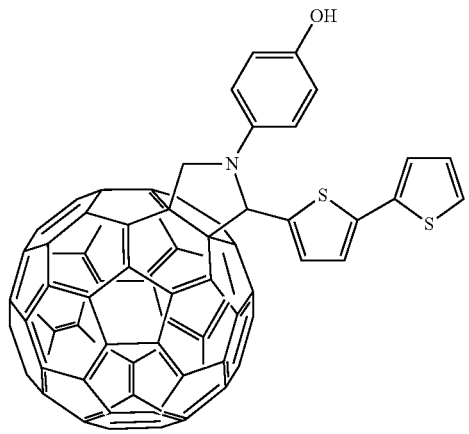

(10)

[Step 2] Synthesis of Fullerene Derivative Having One Structure 108

The fullero pyrrolidine (100 mg, 0.10 mmol), di-tert-butyl dicarbonate (214 mg, 0.98 mmol), 4-dimethylaminopyridine (120 mg, 0.98 mmol) and toluene (100 mL) were placed in a 200-mL double-necked flask equipped with Gimroth condenser, and stirred for 3 hrs at room temperature (25° C.). After the mixture was stirred, the solvent was removed therefrom by a rotary evaporator. Further, after the product was separated off by silica gel column chromatography with toluene as a solvent, the solvent was removed therefrom by a rotary evaporator to obtain a brown solid (104 mg).

The brown solid was subjected to IR absorption spectrum measurement, LC-MS and element analysis. The results were as follows.

IR Absorption Spectrum Measurement (KBr Tablet Method)

The absorption of OH stretching oscillation was observed at 3,440 cm$^{-1}$ disappeared, an absorption of C—H stretching oscillation and an absorption of C=O stretching oscillation were observed at 2,920 cm$^{-1}$ and 1,750 cm$^{-1}$, respectively.

LC-MS (Developing Solvent: Toluene)

m/z=1119 (theoretical value: 1120.17)

Element Analysis

C=86.7% (theoretical value: 86.85%)

H=1.7% (theoretical value: 1.89%)

N=1.2% (theoretical value: 1.25%)

From the above, the brown solid was found to be a fullerene derivative having one structure 108 (yield rate 94.8%).

Example 6

(Synthesis Example of Fullerene Derivative Having One Structure 109)

[Step 1] Synthesis of Fullero Pyrrolidine

Fullerene $C_{60}$ (250 mg, 0.35 mmol), N-(4-hydroxyphenyl) glycin (585 mg, 3.50 mmol), 2,2':5',2'-terthiophene-5-carboxyaldehyde (484 mg, 1.75 mmol) and chlorobenzene (100 mL) were placed in a 200-mL double-necked flask equipped with Gimroth condenser, and heated to reflux for 3 hrs. After the mixture was cooled to have a room temperature, the solvent was removed therefrom by a rotary evaporator. Further, after the product was separated off by silica gel column chromatography with a mixed solvent in which toluene and ethylacetate are mixed at a ratio of 10 to 1 by volume, the solvent was removed therefrom by a rotary evaporator to obtain a brown solid (112 mg).

The brown solid was subjected to IR absorption spectrum measurement, LC-MS and element analysis. The results were as follows.

IR Absorption Spectrum Measurement (KBr Tablet Method)
An absorption of OH stretching oscillation was observed at 3,440 $cm^{-1}$ LC-MS (Developing Solvent: Toluene)
m/z=1102 (theoretical value: 1102.18)

Element Analysis
C=87.2% (theoretical value: 87.18%)
H=1.2% (theoretical value: 1.37%)
N=1.4% (theoretical value: 1.27%)

From the above, the brown solid was found to be fullero pyrrolidine having the following formula (11) (yield rate 29.4%).

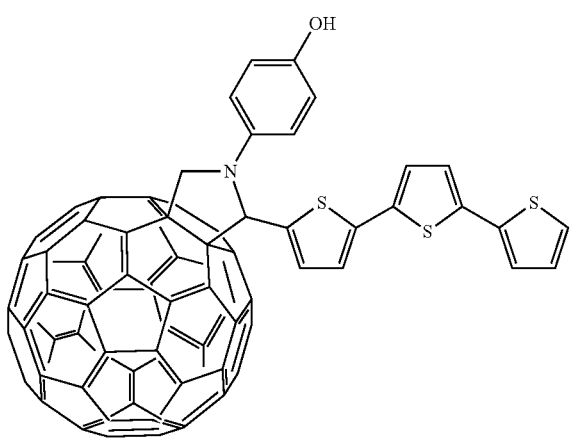

(11)

[Step 2] Synthesis of Fullerene Derivative Having One Structure 109

The fullero pyrrolidine (100 mg, 0.09 mmol), di-tert-butyl dicarbonate (198 mg, 0.91 mmol), 4-dimethylaminopyridine (111 mg, 0.91 mmol) and toluene (100 mL) were placed in a 200-mL double-necked flask equipped with Gimroth condenser, and stirred for 3 hrs at room temperature (25° C.). After the mixture was stirred, the solvent was removed therefrom by a rotary evaporator. Further, after the product was separated off by silica gel column chromatography with toluene as a solvent, the solvent was removed therefrom by a rotary evaporator to obtain a brown solid (106 mg).

The brown solid was subjected to IR absorption spectrum measurement, LC-MS and element analysis. The results were as follows.

IR Absorption Spectrum Measurement (KBr Tablet Method)
The absorption of OH stretching oscillation was observed at 3,440 $cm^{-1}$ disappeared, an absorption of C—H stretching oscillation and an absorption of C=O stretching oscillation were observed at 2,920 $cm^{-1}$ and 1,750 $cm^{-1}$, respectively.

LC-MS (Developing Solvent: Toluene)
m/z=1201 (theoretical value: 1202.29)

Element Analysis
C=84.8% (theoretical value: 84.91%)
H=1.9% (theoretical value: 1.93%)
N=1.1% (theoretical value: 1.16%)

From the above, the brown solid was found to be a fullerene derivative having one structure 109 (yield rate 96.8%).

Example 7

(Synthesis Example of Fullerene Derivative Having Two Structures 73)

[Step 1] Synthesis of Fullero Pyrrolidine

Fullerene $C_{60}$ (250 mg, 0.35 mmol), N-(4-hydroxyphenyl) glycin (585 mg, 3.50 mmol), 3,4-dimethoxybenzaldehyde (291 mg, 1.75 mmol) and chlorobenzene (100 mL) were placed in a 200-mL double-necked flask equipped with Gimroth condenser, and heated to reflux for 6 hrs. After the mixture was cooled to have a room temperature, the solvent was removed therefrom by a rotary evaporator. Further, after the product was separated off by silica gel column chromatography with a mixed solvent in which toluene and ethylacetate are mixed at a ratio of 10 to 1 by volume, the solvent was removed therefrom by a rotary evaporator to obtain a brown solid (98 mg).

The brown solid was subjected to IR absorption spectrum measurement, LC-MS and element analysis. The results were as follows.

IR Absorption Spectrum Measurement (KBr Tablet Method)
An absorption of OH stretching oscillation was observed at 3,440 $cm^{-1}$ LC-MS (Developing Solvent: Toluene)
m/z=1262 (theoretical value: 1263.26)

Element Analysis
C=87.4% (theoretical value: 87.47%)
H=2.6% (theoretical value: 2.71%)
N=2.2% (theoretical value: 2.22%)

From the above, the brown solid was found to be fullero pyrrolidine having the following formula (13) (yield rate 22.4%).

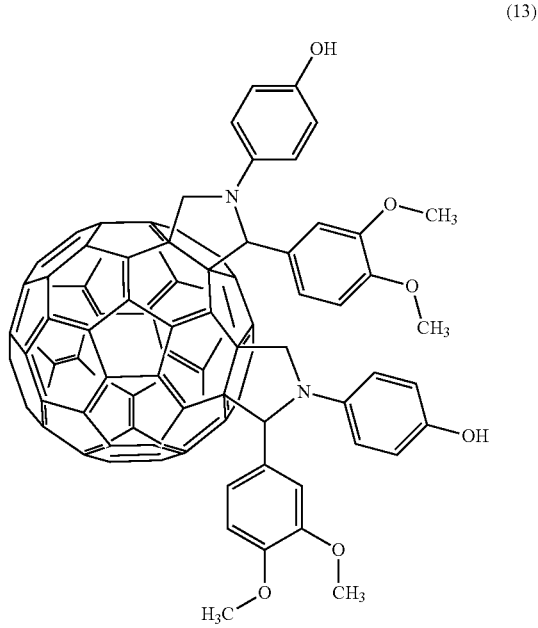

(13)

[Step 2] Synthesis of Fullerene Derivative Having Two Structures 73

The fullero pyrrolidine (100 mg, 0.08 mmol), di-tert-butyl dicarbonate (173 mg, 0.79 mmol), 4-dimethylaminopyridine (97 mg, 0.79 mmol) and toluene (100 mL) were placed in a 200-mL double-necked flask equipped with Gimroth condenser, and stirred for 3 hrs at room temperature (25° C.). After the mixture was stirred, the solvent was removed therefrom by a rotary evaporator. Further, after the product was separated off by silica gel column chromatography with toluene as a solvent, the solvent was removed therefrom by a rotary evaporator to obtain a brown solid (108 mg).

The brown solid was subjected to IR absorption spectrum measurement, LC-MS and element analysis. The results were as follows.

IR Absorption Spectrum Measurement (KBr Tablet Method)

The absorption of OH stretching oscillation was observed at 3,440 cm$^{-1}$ disappeared, an absorption of C—H stretching oscillation and an absorption of C=O stretching oscillation were observed at 2,920 cm$^{-1}$ and 1,750 cm$^{-1}$, respectively.

LC-MS (Developing Solvent: Toluene)

m/z=1463 (theoretical value: 1463.50)

Element Analysis

C=83.7% (theoretical value: 83.71%)

H=3.3% (theoretical value: 3.44%)

N=2.0% (theoretical value: 1.91%)

From the above, the brown solid was found to be a fullerene derivative having two structures 73 (yield rate 92.8%).

Reference Example 1

Synthesis Example of Fullerene Derivative Having One Structure 4

[Step 1] Synthesis of Fullero Pyrrolidine

Fullerene $C_{60}$ (250 mg, 0.35 mmol), N-(4-hydroxyphenyl) glycin (585 mg, 3.50 mmol), butylaldehyde (126 mg, 1.75 mmol) and chlorobenzene (100 mL) were placed in a 200-mL double-necked flask equipped with Gimroth condenser, and heated to reflux for 3 hrs. After the mixture was cooled to have a room temperature, the solvent was removed therefrom by a rotary evaporator. Further, after the product was separated off by silica gel column chromatography with a mixed solvent in which toluene and ethylacetate are mixed at a ratio of 10 to 1 by volume, the solvent was removed therefrom by a rotary evaporator to obtain a brown solid (101 mg).

The brown solid was subjected to IR absorption spectrum measurement, LC-MS and element analysis. The results were as follows.

IR Absorption Spectrum Measurement (KBr Tablet Method)

An absorption of OH stretching oscillation was observed at 3,440 cm$^{-1}$

LC-MS (Developing Solvent: Toluene)

m/z=897 (theoretical value: 897.88)

Element Analysis

C=95.0% (theoretical value: 94.97%)

H=1.5% (theoretical value: 1.68%)

N=1.5% (theoretical value: 1.56%)

From the above, the brown solid was found to be fullero pyrrolidine having the following formula (1) (yield rate 32.3%).

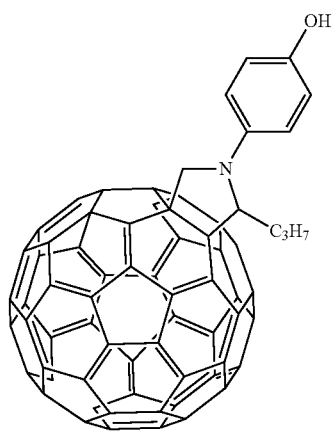

(1)

[Step 2] Synthesis of Fullerene Derivative having two structures 4

The fullero pyrrolidine (100 mg, 0.11 mmol), di-tert-butyl dicarbonate (243 mg, 1.11 mmol), 4-dimethylaminopyridine (136 mg, 1.11 mmol) and toluene (100 mL) were placed in a 200-mL double-necked flask equipped with Gimroth condenser, and stirred for 3 hrs at room temperature (25° C.). After the mixture was stirred, the solvent was removed therefrom by a rotary evaporator. Further, after the product was separated off by silica gel column chromatography with toluene as a solvent, the solvent was removed therefrom by a rotary evaporator to obtain a brown solid (105 mg).

The brown solid was subjected to IR absorption spectrum measurement, LC-MS and element analysis. The results were as follows.

IR Absorption Spectrum Measurement (KBr Tablet Method)

The absorption of OH stretching oscillation was observed at 3,440 cm$^{-1}$ disappeared, an absorption of C—H stretching oscillation and an absorption of C=O stretching oscillation were observed at 2,920 cm$^{-1}$ and 1,750 cm$^{-1}$, respectively.

LC-MS (Developing Solvent: Toluene)

m/z=998 (theoretical value: 998.00)

Element Analysis

C=91.4% (theoretical value: 91.46%)

H=2.2% (theoretical value: 2.32%)

N=1.6% (theoretical value: 1.40%)

From the above, the brown solid was found to be a fullerene derivative having one structure 4 (yield rate 94.1%).

Reference Example 2

Synthesis Example of Fullerene Derivative Having One Structure 5

[Step 1] Synthesis of Fullero Pyrrolidine

Fullerene $C_{60}$ (250 mg, 0.35 mmol), N-(4-hydroxyphenyl) glycin (585 mg, 3.50 mmol), isobutylaldehyde (126 mg, 1.75 mmol) and chlorobenzene (100 mL) were placed in a 200-mL double-necked flask equipped with Gimroth condenser, and heated to reflux for 3 hrs. After the mixture was cooled to have a room temperature, the solvent was removed therefrom by a rotary evaporator. Further, after the product was separated off by silica gel column chromatography with a mixed solvent in which toluene and ethylacetate are mixed at a ratio of 10 to 1 by volume, the solvent was removed therefrom by a rotary evaporator to obtain a brown solid (104 mg).

The brown solid was subjected to IR absorption spectrum measurement, LC-MS and element analysis. The results were as follows.

IR Absorption Spectrum Measurement (KBr Tablet Method)
An absorption of OH stretching oscillation was observed at 3,440 cm$^{-1}$
LC-MS (Developing Solvent: Toluene)
m/z=897 (theoretical value: 897.88)
Element Analysis
C=94.80% (theoretical value: 94.97%)
H=1.6% (theoretical value: 1.68%)
N=1.5% (theoretical value: 1.56%)
From the above, the brown solid was found to be fullero pyrrolidine having the following formula (2) (yield rate 33.4%).

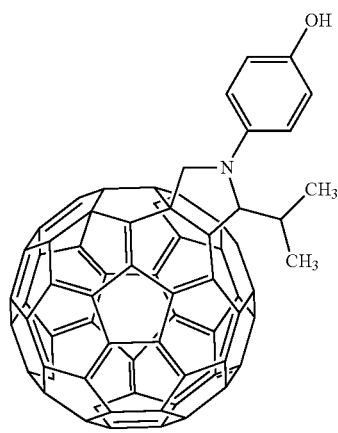

(2)

[Step 2] Synthesis of Fullerene Derivative Having Two Structures 5
The fullero pyrrolidine (100 mg, 0.11 mmol), di-tert-butyl dicarbonate (243 mg, 1.11 mmol), 4-dimethylaminopyridine (136 mg, 1.11 mmol) and toluene (100 mL) were placed in a 200-mL double-necked flask equipped with Gimroth condenser, and stirred for 3 hrs at room temperature (25° C.). After the mixture was stirred, the solvent was removed therefrom by a rotary evaporator. Further, after the product was separated off by silica gel column chromatography with toluene as a solvent, the solvent was removed therefrom by a rotary evaporator to obtain a brown solid (106 mg).
The brown solid was subjected to IR absorption spectrum measurement, LC-MS and element analysis. The results were as follows.
IR Absorption Spectrum Measurement (KBr Tablet Method)
The absorption of OH stretching oscillation was observed at 3,440 cm$^{-1}$ disappeared, an absorption of C—H stretching oscillation and an absorption of C=O stretching oscillation were observed at 2,920 cm$^{-1}$ and 1,750 cm$^{-1}$, respectively.
LC-MS (Developing Solvent: Toluene)
m/z=998 (theoretical value: 998.00)
Element Analysis
C=91.5% (theoretical value: 91.46%)
H=2.3% (theoretical value: 2.32%)
N=1.5% (theoretical value: 1.40%)
From the above, the brown solid was found to be a fullerene derivative having one structure 5 (yield rate 95.6%).

Reference Example 3

Synthesis Example of Fullerene Derivative Having One Structure 11
[Step 1] Synthesis of Fullero Pyrrolidine
Fullerene C$_{60}$ (250 mg, 0.35 mmol), N-(4-hydroxyphenyl) glycin (585 mg, 3.50 mmol), heptoaldehyde (200 mg, 1.75 mmol) and chlorobenzene (100 mL) were placed in a 200-mL double-necked flask equipped with Gimroth condenser, and heated to reflux for 3 hrs. After the mixture was cooled to have a room temperature, the solvent was removed therefrom by a rotary evaporator. Further, after the product was separated off by silica gel column chromatography with a mixed solvent in which toluene and ethylacetate are mixed at a ratio of 10 to 1 by volume, the solvent was removed therefrom by a rotary evaporator to obtain a brown solid (104 mg).
The brown solid was subjected to IR absorption spectrum measurement, LC-MS and element analysis. The results were as follows.
IR Absorption Spectrum Measurement (KBr Tablet Method)
An absorption of OH stretching oscillation was observed at 3,440 cm$^{-1}$
LC-MS (Developing Solvent: Toluene)
m/z=939 (theoretical value: 939.96)
Element Analysis
C=94.40% (theoretical value: 94.56%)
H=2.2% (theoretical value: 2.25%)
N=1.6% (theoretical value: 1.49%)
From the above, the brown solid was found to be fullero pyrrolidine having the following formula (3) (yield rate 30.9%).

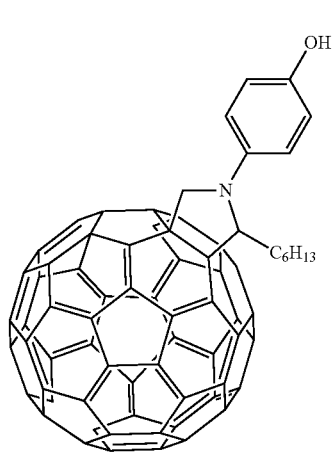

(3)

[Step 2] Synthesis of Fullerene Derivative having two structures 11
The fullero pyrrolidine (100 mg, 0.11 mmol), di-tert-butyl dicarbonate (232 mg, 1.06 mmol), 4-dimethylaminopyridine (130 mg, 1.06 mmol) and toluene (100 mL) were placed in a 200-mL double-necked flask equipped with Gimroth condenser, and stirred for 3 hrs at room temperature (25° C.). After the mixture was stirred, the solvent was removed therefrom by a rotary evaporator. Further, after the product was separated off by silica gel column chromatography with toluene as a solvent, the solvent was removed therefrom by a rotary evaporator to obtain a brown solid (101 mg).
The brown solid was subjected to IR absorption spectrum measurement, LC-MS and element analysis. The results were as follows.
IR Absorption Spectrum Measurement (KBr Tablet Method)
The absorption of OH stretching oscillation was observed at 3,440 cm$^{-1}$ disappeared, an absorption of C—H stretching oscillation and an absorption of C=O stretching oscillation were observed at 2,920 cm$^{-1}$ and 1,750 cm$^{-1}$, respectively.
LC-MS (Developing Solvent: Toluene)
m/z=1040 (theoretical value: 1040.08)

Element Analysis
C=91.4% (theoretical value: 91.23%)
H=2.7% (theoretical value: 2.81%)
N=1.3% (theoretical value: 1.35%)
From the above, the brown solid was found to be a fullerene derivative having one structure 11 (yield rate 96.0%).

Reference Example 4

Synthesis Example of Fullerene Derivative Having One Structure 14
[Step 1] Synthesis of Fullero Pyrrolidine
Fullerene $C_{60}$ (250 mg, 0.35 mmol), N-(4-hydroxyphenyl) glycin (585 mg, 3.50 mmol), decanal (273 mg, 1.75 mmol) and chlorobenzene (100 mL) were placed in a 200-mL double-necked flask equipped with Gimroth condenser, and heated to reflux for 3 hrs. After the mixture was cooled to have a room temperature, the solvent was removed therefrom by a rotary evaporator. Further, after the product was separated off by silica gel column chromatography with a mixed solvent in which toluene and ethylacetate are mixed at a ratio of 10 to 1 by volume, the solvent was removed therefrom by a rotary evaporator to obtain a brown solid (115 mg).

The brown solid was subjected to IR absorption spectrum measurement, LC-MS and element analysis. The results were as follows.
IR Absorption Spectrum Measurement (KBr Tablet Method)
An absorption of OH stretching oscillation was observed at 3,440 $cm^{-1}$
LC-MS (Developing Solvent: Toluene)
m/z=981 (theoretical value: 982.04)
Element Analysis
C=94.40% (theoretical value: 94.17%)
H=2.8% (theoretical value: 2.77%)
N=1.4% (theoretical value: 1.43%)
From the above, the brown solid was found to be fullero pyrrolidine having the following formula (4) (yield rate 33.6%).

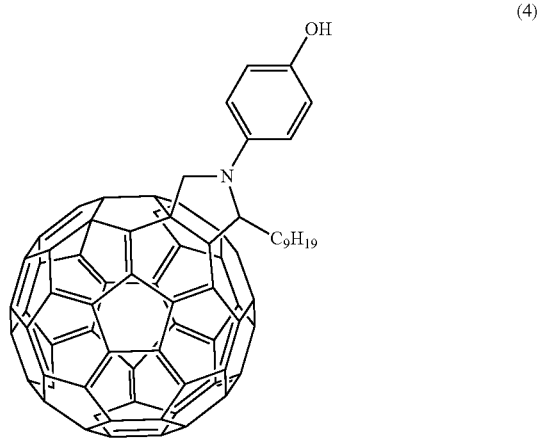

(4)

[Step 2] Synthesis of Fullerene Derivative having two structures 14
The fullero pyrrolidine (100 mg, 0.11 mmol), di-tert-butyl dicarbonate (222 mg, 1.02 mmol), 4-dimethylaminopyridine (124 mg, 1.02 mmol) and toluene (100 mL) were placed in a 200-mL double-necked flask equipped with Gimroth condenser, and stirred for 3 hrs at room temperature (25° C.). After the mixture was stirred, the solvent was removed therefrom by a rotary evaporator. Further, after the product was separated off by silica gel column chromatography with toluene as a solvent, the solvent was removed therefrom by a rotary evaporator to obtain a brown solid (106 mg).

The brown solid was subjected to IR absorption spectrum measurement, LC-MS and element analysis. The results were as follows.
IR Absorption Spectrum Measurement (KBr Tablet Method)
The absorption of OH stretching oscillation was observed at 3,440 $cm^{-1}$ disappeared, an absorption of C—H stretching oscillation and an absorption of C=O stretching oscillation were observed at 2,920 $cm^{-1}$ and 1,750 $cm^{-1}$, respectively.
LC-MS (Developing Solvent: Toluene)
m/z=1081 (theoretical value: 1082.16)
Element Analysis
C=91.0% (theoretical value: 91.01%)
H=3.1% (theoretical value: 3.26%)
N=1.4% (theoretical value: 1.29%)
From the above, the brown solid was found to be a fullerene derivative having one structure 14 (yield rate 95.8%).

Reference Example 5

Synthesis Example of Fullerene Derivative Having One Structure 17
[Step 1] Synthesis of Fullero Pyrrolidine
Fullerene $C_{60}$ (250 mg, 0.35 mmol), N-(4-hydroxyphenyl) glycin (585 mg, 3.50 mmol), tridecanal (347 mg, 1.75 mmol) and chlorobenzene (100 mL) were placed in a 200-mL double-necked flask equipped with Gimroth condenser, and heated to reflux for 3 hrs. After the mixture was cooled to have a room temperature, the solvent was removed therefrom by a rotary evaporator. Further, after the product was separated off by silica gel column chromatography with a mixed solvent in which toluene and ethylacetate are mixed at a ratio of 10 to 1 by volume, the solvent was removed therefrom by a rotary evaporator to obtain a brown solid (125 mg).

The brown solid was subjected to IR absorption spectrum measurement, LC-MS and element analysis. The results were as follows.
IR Absorption Spectrum Measurement (KBr Tablet Method)
An absorption of OH stretching oscillation was observed at 3,440 $cm^{-1}$
LC-MS (Developing Solvent: Toluene)
m/z=1023 (theoretical value: 1024.12)
Element Analysis
C=93.6% (theoretical value: 93.82%)
H=3.0% (theoretical value: 3.25%)
N=1.4% (theoretical value: 1.37%)
From the above, the brown solid was found to be fullero pyrrolidine having the following formula (5) (yield rate 35.1%).

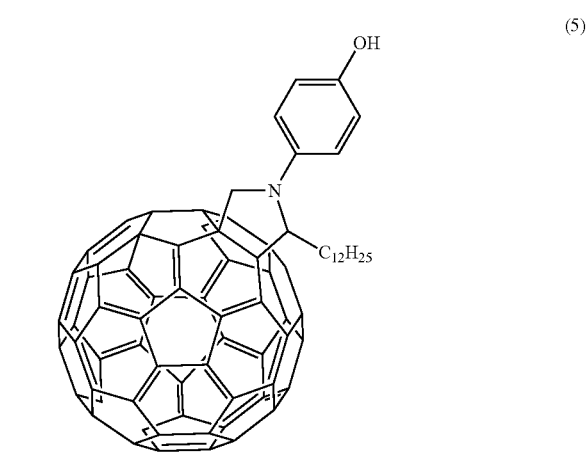

(5)

[Step 2] Synthesis of Fullerene Derivative Having Two Structures 17

The fullero pyrrolidine (100 mg, 0.11 mmol), di-tert-butyl dicarbonate (213 mg, 0.98 mmol), 4-dimethylaminopyridine (119 mg, 0.98 mmol) and toluene (100 mL) were placed in a 200-mL double-necked flask equipped with Gimroth condenser, and stirred for 3 hrs at room temperature (25° C.). After the mixture was stirred, the solvent was removed therefrom by a rotary evaporator. Further, after the product was separated off by silica gel column chromatography with toluene as a solvent, the solvent was removed therefrom by a rotary evaporator to obtain a brown solid (104 mg).

The brown solid was subjected to IR absorption spectrum measurement, LC-MS and element analysis. The results were as follows.

IR Absorption Spectrum Measurement (KBr Tablet Method)

The absorption of OH stretching oscillation was observed at 3,440 cm$^{-1}$ disappeared, an absorption of C—H stretching oscillation and an absorption of C=O stretching oscillation were observed at 2,920 cm$^{-1}$ and 1,750 cm$^{-1}$, respectively.

LC-MS (Developing Solvent: Toluene)

m/z=1123 (theoretical value: 1124.24)

Element Analysis

C=90.7% (theoretical value: 90.81%)

H=3.4% (theoretical value: 3.68%)

N=1.4% (theoretical value: 1.25%)

From the above, the brown solid was found to be a fullerene derivative having one structure 17 (yield rate 95.0%).

Reference Example 6

Synthesis Example of Fullerene Derivative Having Two Structures 1

[Step 1] Synthesis of Fullero Pyrrolidine

Fullerene $C_{60}$ (250 mg, 0.35 mmol), N-(4-hydroxyphenyl) glycin (585 mg, 3.50 mmol), paraformaldehyde (53 mg) and chlorobenzene (100 mL) were placed in a 200-mL double-necked flask equipped with Gimroth condenser, and heated to reflux for 6 hrs. After the mixture was cooled to have a room temperature, the solvent was removed therefrom by a rotary evaporator. Further, after the product was separated off by silica gel column chromatography with a mixed solvent in which toluene and ethylacetate are mixed at a ratio of 10 to 1 by volume, the solvent was removed therefrom by a rotary evaporator to obtain a brown solid (87 mg).

The brown solid was subjected to IR absorption spectrum measurement, LC-MS and element analysis. The results were as follows.

IR Absorption Spectrum Measurement (KBr Tablet Method)

An absorption of OH stretching oscillation was observed at 3,440 cm$^{-1}$

LC-MS (Developing Solvent: Toluene)

m/z=990 (theoretical value: 990.97)

Element Analysis

C=92.2% (theoretical value: 92.11%)

H=1.8% (theoretical value: 1.83%)

N=2.9% (theoretical value: 2.83%)

From the above, the brown solid was found to be fullero pyrrolidine having the following formula (12) (yield rate 25.3%).

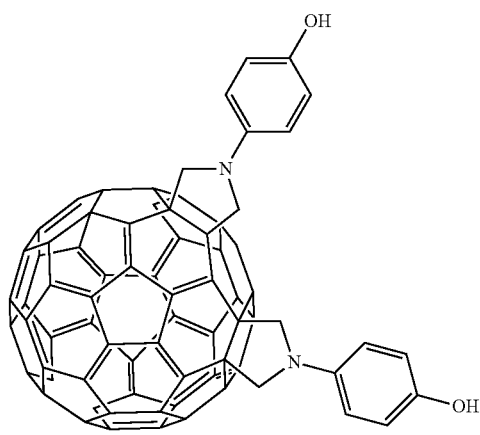

(12)

[Step 2] Synthesis of Fullerene Derivative Having Two Structures 1

The fullero pyrrolidine (100 mg, 0.11 mmol), di-tert-butyl dicarbonate (220 mg, 1.01 mmol), 4-dimethylaminopyridine (123 mg, 1.01 mmol) and toluene (100 mL) were placed in a 200-mL double-necked flask equipped with Gimroth condenser, and stirred for 3 hrs at room temperature (25° C.). After the mixture was stirred, the solvent was removed therefrom by a rotary evaporator. Further, after the product was separated off by silica gel column chromatography with toluene as a solvent, the solvent was removed therefrom by a rotary evaporator to obtain a brown solid (116 mg).

The brown solid was subjected to IR absorption spectrum measurement, LC-MS and element analysis. The results were as follows.

IR Absorption Spectrum Measurement (KBr Tablet Method)

The absorption of OH stretching oscillation was observed at 3,440 cm$^{-1}$ disappeared, an absorption of C—H stretching oscillation and an absorption of C=O stretching oscillation were observed at 2,920 cm$^{-1}$ and 1,750 cm$^{-1}$, respectively.

LC-MS (Developing Solvent: Toluene)

m/z=1190 (theoretical value: 1191.20)

Element Analysis

C=86.6% (theoretical value: 86.71%)

H=2.8% (theoretical value: 2.88%)

N=2.3% (theoretical value: 2.35%)

From the above, the brown solid was found to be a fullerene derivative having two structures 1 (yield rate 96.2%).

Example 8

Solubilities of the fullerene derivatives obtained in Examples 1 to 7 and Reference Examples 1 to 6, and PCBM (nanom spectra E100 from Frontier Carbon Corp.) as a Comparative Example in chloroform were evaluated by the following method. A 0.1 mM chloroform solution and a 1.0 mM chloroform solution of each of the fullerene derivatives and the PCBM were prepared, and diluted fivefold with THF for HPLC. Ten (10) μL of the diluted solution was analyzed by a high-speed liquid chromatograph (LC-2010HT from Shimadzu Corp.; developing solvent: THF/ion-exchanged water=60/40; analysis time: 60 min; and detection wavelength: 254 nm) to prepare a chromatogram. Standard curves of the known concentrations (0.1 mM and 1.0 mM) were obtained therefrom. Next, a saturated chloroform solution of each of the fullerene derivatives and the PCBM were prepared at 25° C. After the saturated solution was filtered with a 0.45 µm filter, it was diluted hundredfold with THF for HPLC. Ten (10) µL of the diluted solution was analyzed by the same method mentioned above to prepare a chromatogram. A weight of each of the fullerene derivative and the PCBM dissolved in 1 mL of chloroform was determined as solubility using a peak area value of the chromatogram from the saturated solution and the standard curves. The results are shown in Table 2.

TABLE 2

| | Weight of Fullerene Derivative in 1 ml of Chloroform |
|---|---|
| Example 1 | 46 mg |
| Example 2 | 75 mg |
| Example 3 | 55 mg |
| Example 4 | 35 mg |
| Example 5 | 55 mg |
| Example 6 | 41 mg |
| Example 7 | 89 mg |
| Reference Example 1 | 29 mg |
| Reference Example 2 | 25 mg |
| Reference Example 3 | 50 mg |
| Reference Example 4 | 66 mg |
| Reference Example 5 | 89 mg |
| Reference Example 6 | 80 mg |
| PCBM | 18 mg |

This proves the fullerene derivative of the present invention has higher solubility than PCBM.

Example 9

The following is an example of an organic solar battery as an application of the fullerene derivative of the present invention. On a washed and patterned glass plate with an ITO electrode, a solution in which 2 g of PEDOT/PSS[poly(3,4-ethyleneoxythiophene)/poly(styrenesulfonate)] (CLEVIOS PHSO0 from H.C. Starck GmbH) and 5 g of 2-propanol are mixed was coated by a spin coating method at 1100 rpm, and the coated glass plate was heated on a hot plate at 140° C. for 10 min to form a 40 nm thick positive hole takeout layer thereon. Next, 1.4 g of chloroform, 25 mg of low-molecular-weight semiconductive compound having the following formula 76 disclosed in PCT Japanese published national phase application No. 2011-501743 and 20 mg of each of the fullerene derivative (having a HPLC purity not less than 99.5%) which is refined and isolated by HPLC (developing solvent: chloroform) were stirred a 45° C. for 3 hrs in a nitrogen atmosphere to prepare a coating liquid. On the coated glass plate, the coating liquid was coated by a spin coating method at 500 rpm for 60 sec, and the coated glass plate was heated on a hot plate at 150° C. for 5 min to form a 150 nm thick mixed layer thereon. The thus prepared glass plate was set in a vacuum evaporator to evaporate a 40 nm thick aluminum electrode thereon to prepare an organic solar battery.

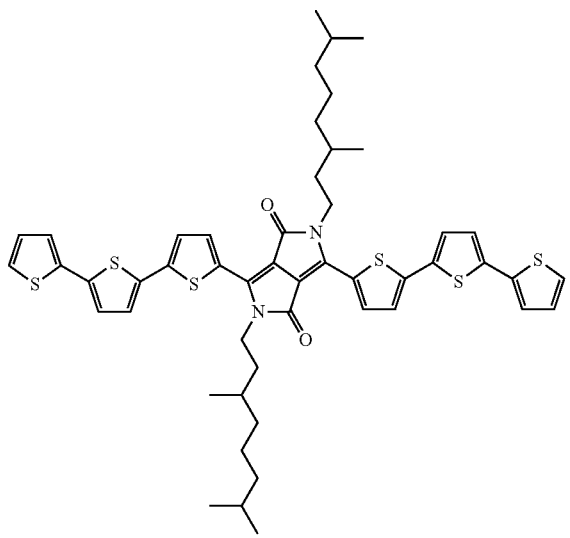 [SMILES: CC(C)CCCC(C)CCN1C(=O)C2=C(c3ccc(-c4ccc(-c5cccs5)s4)s3)N(CCC(C)CCCC(C)C)C(=O)C2=C1c1ccc(-c2ccc(-c3cccs3)s2)s1]

Light having 100 mW/cm² intensity was emitted from a solar simulator (AM1.5G filter) to the organic solar battery, a mask having an effective area of 0.16 cm² was overlapped on a light receiver, and a current-voltage property between the ITO electrode and the aluminum electrode was measured by a solar battery evaluation system (As-510-PV from NF Corp.) to determine an exchange efficiency to evaluate the solar battery. The results of photoelectric conversion efficiency and open circuit voltage are shown in Table 3.

TABLE 3

| | Photoelectric Conversion Efficiency | Open Circuit Voltage |
|---|---|---|
| Reference Example 1 | 0.85% | 0.43 V |
| Reference Example 2 | 0.84% | 0.42 V |
| Reference Example 3 | 0.87% | 0.44 V |
| Reference Example 4 | 0.88% | 0.45 V |
| Reference Example 5 | 0.89% | 0.45 V |
| Example 1 | 1.04% | 0.53 V |
| Example 2 | 1.16% | 0.59 V |
| Example 3 | 1.09% | 0.56 V |
| Example 4 | 1.02% | 0.52 V |
| Example 5 | 1.01% | 0.51 V |
| Example 6 | 1.00% | 0.50 V |
| Reference Example 6 | 1.14% | 0.62 V |
| Example 7 | 1.27% | 0.69 V |

This proves the fullerene derivative of the present invention is preferably used as an organic solar battery, and has high conversion efficiency with improvement of the open circuit voltage.

Having now fully described the invention, it will be apparent to one of ordinary skill in the art that many changes and modifications can be made thereto without departing from the spirit and scope of the invention as set forth therein.

What is claimed is:

1. A fullerene derivative having 60 or more carbon atoms, wherein said derivative comprises at least one structure of the following formula (I):

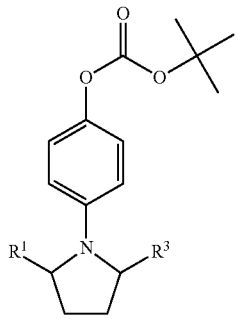

(I)

wherein $R^1$ and $R^3$ independently represent a hydrogen atom, a halogen atom, a substituted or unsubstituted alkyl group, a substituted or unsubstituted alkoxy group, a substituted or unsubstituted aryl group, a substituted or unsubstituted monofunctional heterocyclic group, or a group having the following formula (II) or (III), and at least one of $R^1$ and $R^3$ is a group having the formula (II) or (III):

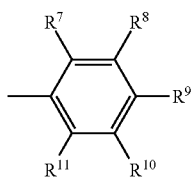

(II)

wherein $R^7$, $R^8$, $R^9$, $R^{10}$ and $R^{11}$ independently represent a hydrogen atom, a halogen atom, a substituted or unsubstituted alkyl group, a substituted or unsubstituted alkoxy group, a substituted or unsubstituted alkoxycarbonyloxy group, a substituted or unsubstituted aryl group, a substituted or unsubstituted monofunctional heterocyclic group, or a methoxy group, and at least one or more thereof are methoxy groups;

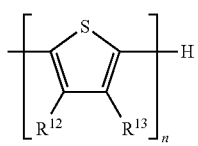

(III)

wherein $R^{12}$ and $R^{13}$ independently represent a hydrogen atom, a halogen atom, a substituted or unsubstituted alkyl group, a substituted or unsubstituted alkoxy group, a substituted or unsubstituted aryl group, or a substituted or unsubstituted monofunctional heterocyclic group; and n represents an integer of from 1 to 8.

2. A method of preparing the fullerene derivative according to claim 1, comprising:

reacting a precursor of the fullerene derivative having 60 or more carbon atoms, said precursor comprising at least one structure of the following formula (IV):

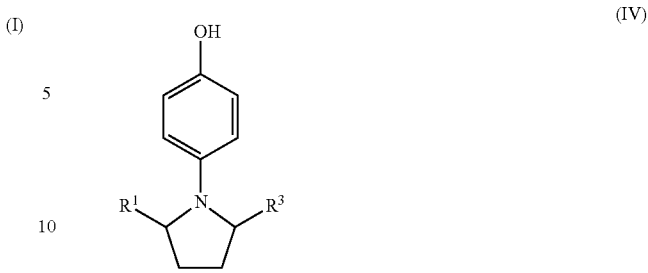

(IV)

wherein $R^1$ and $R^3$ independently represent a hydrogen atom, a halogen atom, a substituted or unsubstituted alkyl group, a substituted or unsubstituted alkoxy group, a substituted or unsubstituted aryl group, a substituted or unsubstituted monofunctional heterocyclic group, or a group having the formula (II) or (III), and at least one of $R^1$ and $R^3$ is a group having the formula (II) or (III); and a diesterpyrocarbonate having the following formula (V):

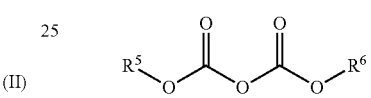

(V)

wherein $R^5$ and $R^6$ represent a tert-butyl group.

3. A fullerene derivative having 60 or more carbon atoms, wherein said derivative comprises at least one structure of the following formula(IV):

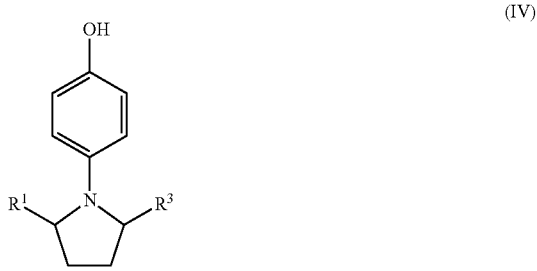

(IV)

wherein $R^1$ and $R^3$ independently represent a hydrogen atom, a halogen atom, a substituted or unsubstituted alkyl group, a substituted or unsubstituted alkoxy group, a substituted or unsubstituted aryl group, a substituted or unsubstituted monofunctional heterocyclic group, or a group having the following formula (II) or (III), and at least one of $R^1$ and $R^3$ is a group having the formula (II) or (III):

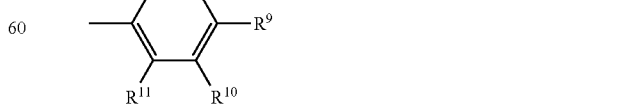

(II)

wherein $R^7$, $R^8$, $R^9$, $R^{10}$ and $R^{11}$ independently represent a hydrogen atom, a halogen atom, a substituted or unsubstituted alkyl group, a substituted or unsubstituted alkoxy group, a substituted or unsubstituted alkoxycarbonyloxy group, a substituted or unsubstituted aryl group, a substituted or unsubstituted monofunctional heterocyclic group, or a methoxy group, and at least one or more thereof are methoxy groups;

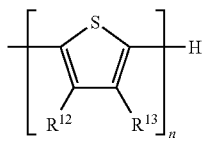
(III)

wherein $R^{12}$ and $R^{13}$ independently represent a hydrogen atom, a halogen atom, a substituted or unsubstituted alkyl group, a substituted or unsubstituted alkoxy group, a substituted or unsubstituted aryl group, or a substituted or unsubstituted monofunctional heterocyclic group; and n represents an integer of from 1 to 8.

4. An organic solar battery comprising the fullerene derivative of claim 1.

5. The fullerene derivative of claim 1, wherein said fullerene derivative having 60 or more carbon atoms is a C60, C70, C76, C78, C80, C82, C84, C86, C88, C90, C92, C94 or C96 fullerene.

6. The method of claim 2, wherein said fullerene derivative having 60 or more carbon atoms is a C60, C70, C76, C78, C80, C82, C84, C86, C88, C90, C92, C94 or C96 fullerene.

7. The fullerene derivative of claim 3, wherein said fullerene derivative having 60 or more carbon atoms is a C60, C70, C76, C78, C80, C82, C84, C86, C88, C90, C92, C94 or C96 fullerene.

8. The organic solar battery of claim 4, wherein said fullerene derivative having 60 or more carbon atoms is a C60, C70, C76, C78, C80, C82, C84, C86, C88, C90, C92, C94 or C96 fullerene.

* * * * *